United States Patent
Lovell et al.

(10) Patent No.: US 10,086,074 B2
(45) Date of Patent: Oct. 2, 2018

(54) COMPOSITIONS AND METHOD FOR LIGHT TRIGGERED RELEASE OF MATERIALS FROM NANOVESICLES

(71) Applicants: The Research Foundation for The State University of New York, Amherst, NY (US); Health Research, Inc., Buffalo, NY (US)

(72) Inventors: Jonathan Lovell, Niagara Falls (CA); Ravindra Pandey, East Amherst, NY (US); Kevin Carter, Amherst, NY (US); Shuai Shao, Amherst, NY (US)

(73) Assignees: The Research Foundation for The State University of New York, Amherst, NY (US); Health Research, Inc., Buffalo, NY (US)

(*) Notice: Subject to any disclaimer, the term of this patent is extended or adjusted under 35 U.S.C. 154(b) by 251 days.

(21) Appl. No.: 14/654,085

(22) PCT Filed: Dec. 19, 2013

(86) PCT No.: PCT/US2013/076471
§ 371 (c)(1),
(2) Date: Jun. 19, 2015

(87) PCT Pub. No.: WO2014/100379
PCT Pub. Date: Jun. 26, 2014

(65) Prior Publication Data
US 2015/0297716 A1    Oct. 22, 2015

Related U.S. Application Data

(60) Provisional application No. 61/739,503, filed on Dec. 19, 2012.

(51) Int. Cl.
| | | |
|---|---|---|
| *A61K 49/00* | (2006.01) | |
| *A61K 41/00* | (2006.01) | |
| *C07D 487/22* | (2006.01) | |
| *A61K 9/127* | (2006.01) | |
| *A61K 31/704* | (2006.01) | |
| *A61K 31/7048* | (2006.01) | |
| *A61N 5/06* | (2006.01) | |

(52) U.S. Cl.
CPC .......... *A61K 41/0028* (2013.01); *A61K 9/127* (2013.01); *A61K 9/1271* (2013.01); *A61K 31/704* (2013.01); *A61K 31/7048* (2013.01); *A61K 41/0071* (2013.01); *A61N 5/062* (2013.01); *C07D 487/22* (2013.01); *A61N 2005/0658* (2013.01)

(58) Field of Classification Search
CPC .............. A61K 41/0028; A61K 9/1271; A61K 41/0071; A61K 9/127; A61N 2005/0658
USPC ........................................................ 424/9.1
See application file for complete search history.

(56) References Cited

U.S. PATENT DOCUMENTS

| | | | |
|---|---|---|---|
| 5,013,556 A | 5/1991 | Woodle et al. | |
| 5,192,549 A | 3/1993 | Barenolz et al. | |
| 8,048,448 B2 | 11/2011 | Ludwig et al. | |
| 9,072,774 B2 * | 7/2015 | Zheng et al. | |
| 2005/0019265 A1 | 1/2005 | Hammer | |
| 2010/0247447 A1 | 9/2010 | Boch et al. | |
| 2011/0052671 A1 * | 3/2011 | Zasadzinski et al. | 424/450 |
| 2011/0318415 A1 | 12/2011 | Li et al. | |

FOREIGN PATENT DOCUMENTS

| | | |
|---|---|---|
| CN | 1088210 | 6/1994 |
| CN | 101573141 | 11/2009 |
| CN | 102573914 | 7/2012 |
| WO | 2009111439 | 9/2009 |
| WO | 2011/044671 A1 | 4/2011 |
| WO | 2012/167350 A1 | 12/2012 |

OTHER PUBLICATIONS

Volodkin et al. Angew. Chem. Int. Ed. 2009, 48, 1807-1809.*
Noiseux et al. J. Biomed. Opt. 2008, 48, 041313-1-041313-11.*
You, J., et al., Exceptionally High Payload of Doxorubicin in Hollow Gold Nanospheres for Near-Infrared Light-Triggered Drug Release, ACS Nano, 2010, vol. 4, No. 2, pp. 1033-1041.
Lovell, J.F., et al., Enzymatic Regioselection for the Synthesis of Biodegradation of Porphysome Nanovesicles, Angewandte Chemie International Edition, 2012, vol. 51, pp. 2429-2433.
Lovell, J.F., et al., Enzymatic Regioselection for the Synthesis of Biodegradation of Porphysome Nanovesicles, Angewandte Chemie, 2012, vol. 124, pp. 2479-2483.

* cited by examiner

*Primary Examiner* — Michael G Hartley
*Assistant Examiner* — Sean R Donohue
(74) *Attorney, Agent, or Firm* — Hodgson Russ LLP

(57) ABSTRACT

Provided are compositions comprising porphyrin-phospholipid nanovesicles (PoP-NVs) which can be loaded with cargo. Methods for release of cargo from the PoP-NVs triggered by near infrared (NIR) light are also disclosed.

15 Claims, 17 Drawing Sheets

COMPOSITIONS AND METHOD FOR LIGHT TRIGGERED RELEASE OF MATERIALS FROM NANOVESICLES

CROSS-REFERENCE TO RELATED APPLICATIONS

This application claims priority to U.S. Provisional patent application No. 61/739,503, filed Dec. 19, 2012, the disclosure of which is incorporated herein by reference.

STATEMENT REGARDING FEDERALLY SPONSORED RESEARCH

This invention was made with government support under contract no. R01EB017270 and DP5OD017898 awarded by the National Institutes of Health. The government has certain rights in the invention.

BACKGROUND OF THE DISCLOSURE

Drug delivery to target tissues can be just as important as the drug being delivered. Several clinically approved nanocarriers have been developed to enhance the biodistribution and efficacy of certain drugs. However, such delivery is hampered by physiological barriers and release kinetics so that biodistribution and bioavailability are almost inevitably sub-optimal. Presently, the most viable approaches for externally triggered cargo release from nanocarriers comprise systems that release their contents when the surrounding temperatures are raised by a few degrees above body temperature by direct or indirect heating. However, such mechanisms are not readily amenable to trigger-side release modulation and the narrow thermal operating window precludes high carrier stability at physiological temperatures.

SUMMARY OF THE DISCLOSURE

The present disclosure provides self-assembled nanoparticles comprising porphyrin-phospholipid conjugates. Nanovesicles comprising the porphyrin-phospholipid compounds of the present disclosure—also referred to herein as porphyrin-phospholipid nanovesicles ("PoP-NVs") or porphyrin-phospholipid liposomes ("PoP-liposomes) provide stable cargo retention in the absence of near infrared (NIR) irradiation (650-1000 nm) radiation, and controlled release of cargo upon exposure to NIR irradiation.

In one aspect, this disclosure provides nanovesicles which comprise a bilayer, said bilayer comprising porphyrin conjugates. The porphyrin conjugates comprise a porphyrin having a alkyl ether side chain, and a phospholipid. In one aspect, the disclosure provides compositions comprising the nanovesicles and a suitable carrier such as a buffer or saline solution.

In one aspect this disclosure provides methods for loading of the nanovesicles with desired cargo and methods for delivery of cargo in vitro or in vivo in a spatially and temporally controlled manner.

Calcein release and solution temperature measured for PoP-NVs a) in the absence or b) in the presence of 150 mW, 658 nm laser irradiation. Temperature in the solution was measured every 30 seconds using a thermocouple.

Figure 5:
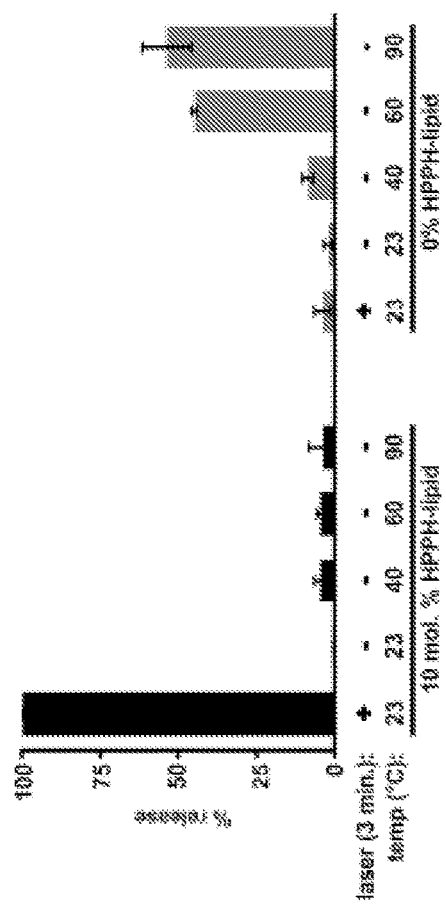
Figure 6:
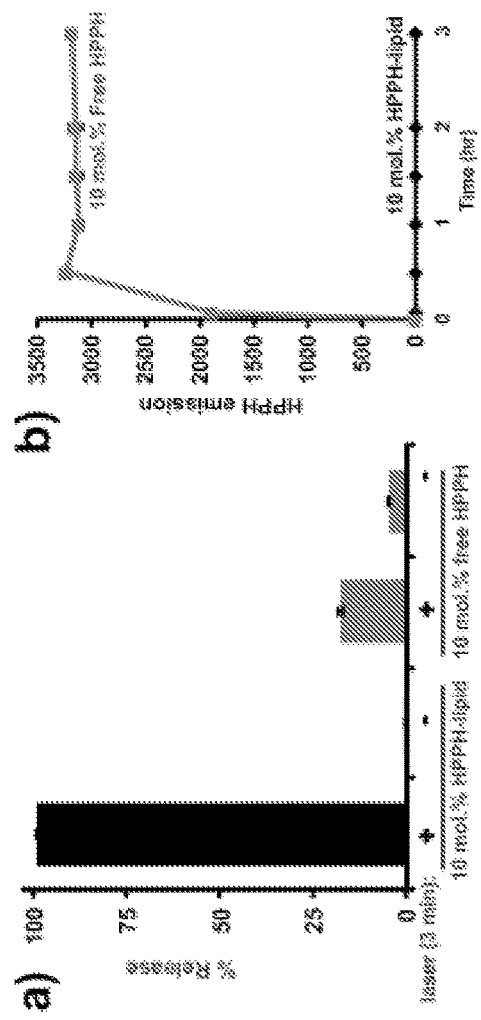

FIG. 5. Demonstration of conferred thermal stability of PoP-NVs. Calcein loaded PoP-NVs doped with or without 10 molar % HPPH phospholipid were incubated for 10 minutes in saline at the indicated temperatures with or without a 3 minute laser pre-treatment FIG. 6. Demonstration of that doping with HPPH phospolipid, but not free HPPH is sufficient for effective light-triggered release. a) Calcein release in NVs formed with 10 molar percent HPPH phospholipid or free HPPH and irradiated with light. b) Rapid serum redistribution of liposomes containing free HPPH, but not HPPH phospholipid as judged by fluorescence unquenching.

Figure 7:
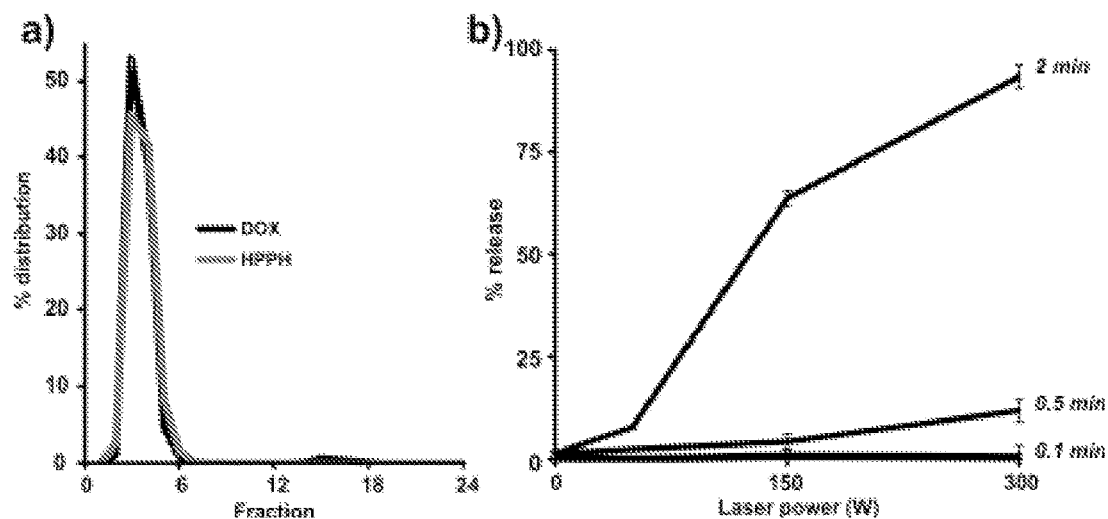

FIG. 7. Example of remote doxorubicin loading and tunable drug release in POP-NVs a) Gel filtration demonstrating active doxorubin loading in PoP-NVs. Over 95% of doxorubicin was loaded when NVs were incubated at a 10:1 lipid to drug ratio at 60° C. for 1 hour. b) Tunable drug release using PoP-NVs. Doxorubicin loaded PoP-NVs were loaded and irradiated at varying times and laser powers in media containing 10% serum. Standard deviation for 3 separate experiments.

Figure 8:
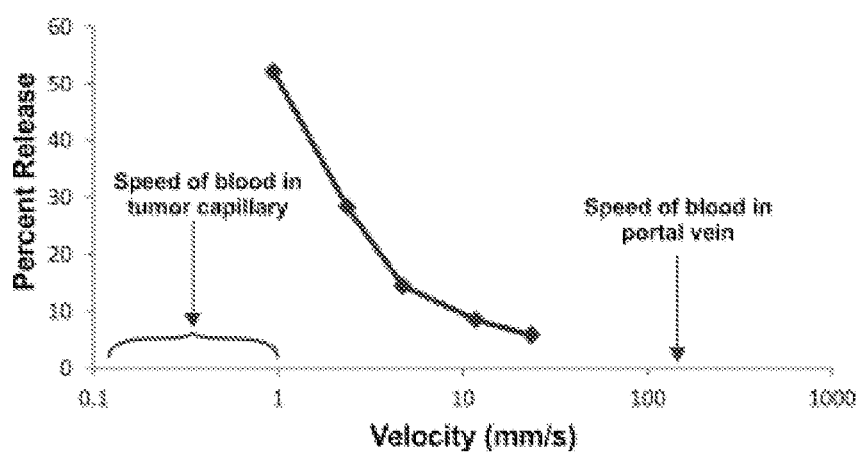

FIG. 8. Demonstration of flow rates affects cargo release from PoP-NVs. Calcein loaded PoP-NVs were moved through capillary tubing at the indicated velocities under irradiation and release was measured following fluid exit from the tubing.

Figure 9:
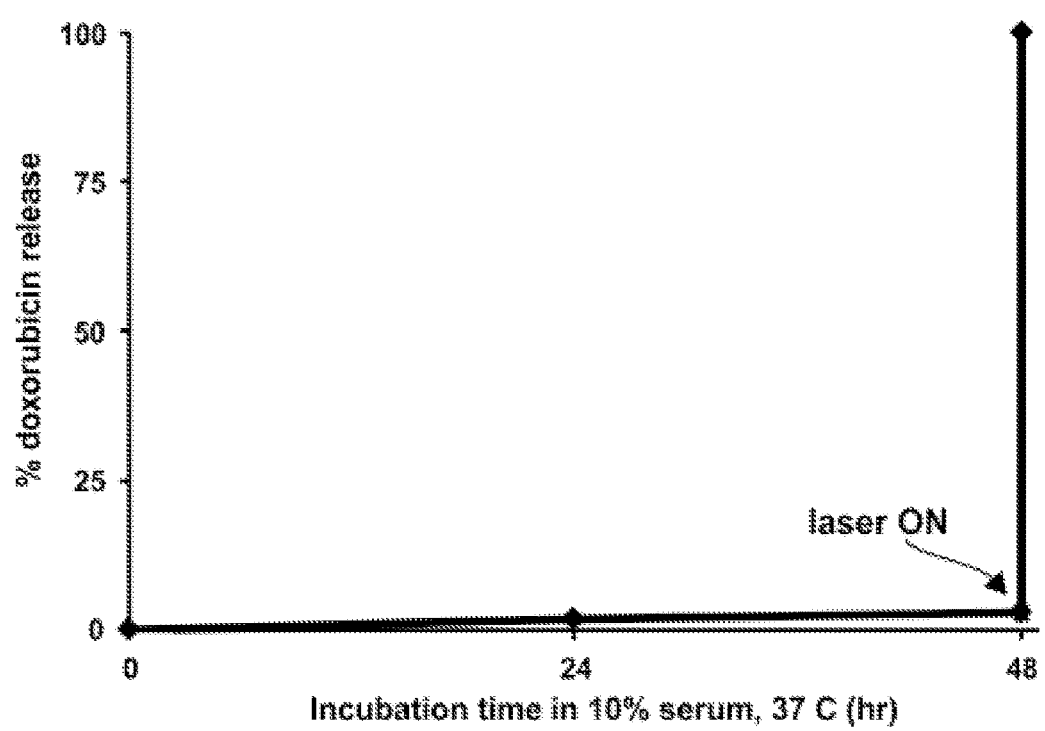

FIG. 9. Example of PoP-NVs were loaded with doxorubicin using an ammonium sulfate gradient and incubated in 10% serum at 37° C. for 2 days. Following incubation, samples were irradiated with 658 nm laser for 5 minutes and release was immediately measured.

Figure 10:
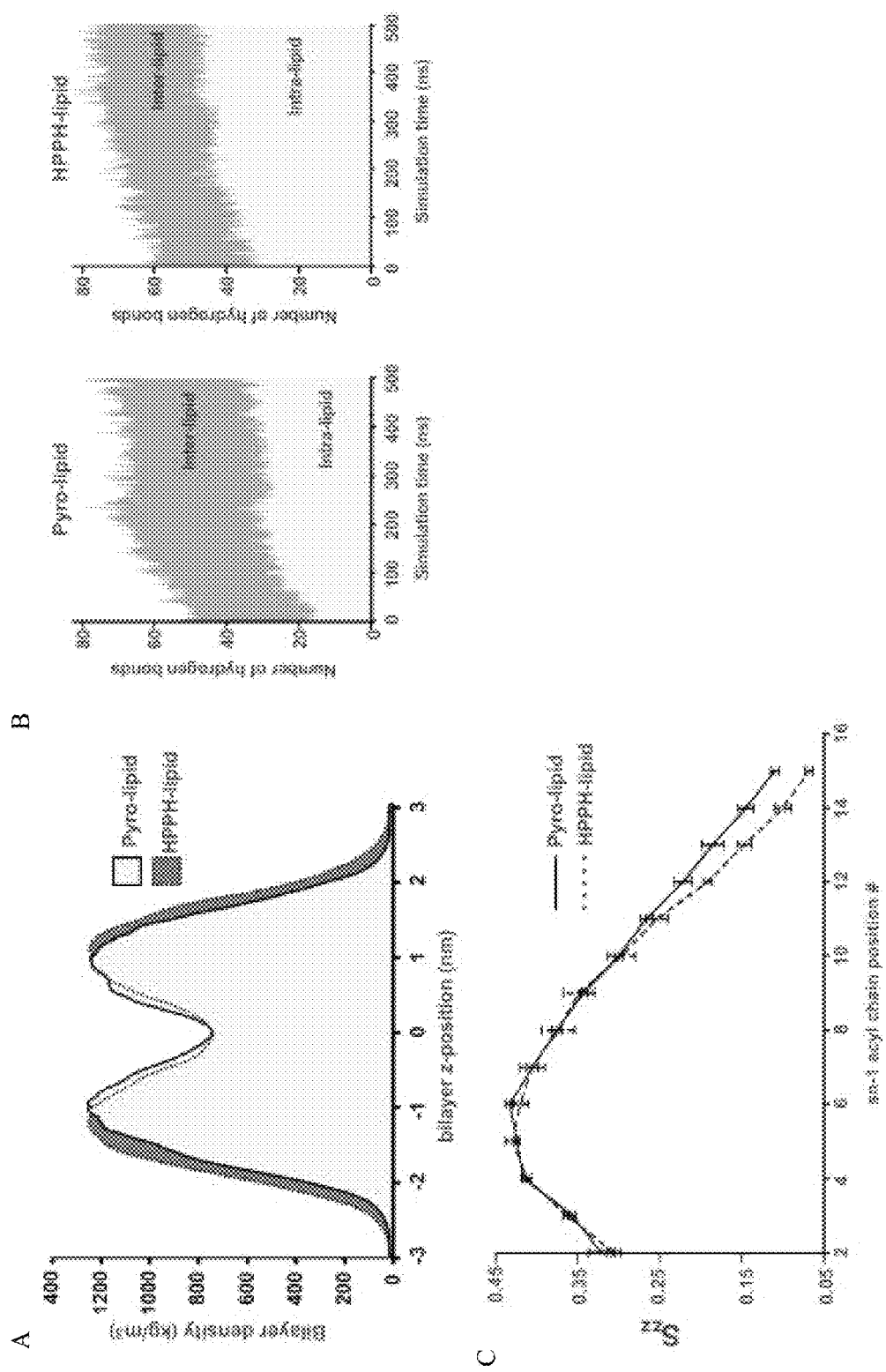

FIG. 10. Example of a) HPPH phospolipid and pyro-lipid density (excluding water contribution) post 150-ns MD (molecular dynamics) simulation. b) Evolution of hydrogen bonds formed during 500 ns MD simulation. Intra- and inter-molecular hydrogen bonds for each type of porphyrin-lipid are indicated. c) Chain order parameter (Szz) for porphyrin-lipids following 500 ns MD simulation. Szz indicates order of lipid chain with respect to bilayer normal vector.

Figure 11:
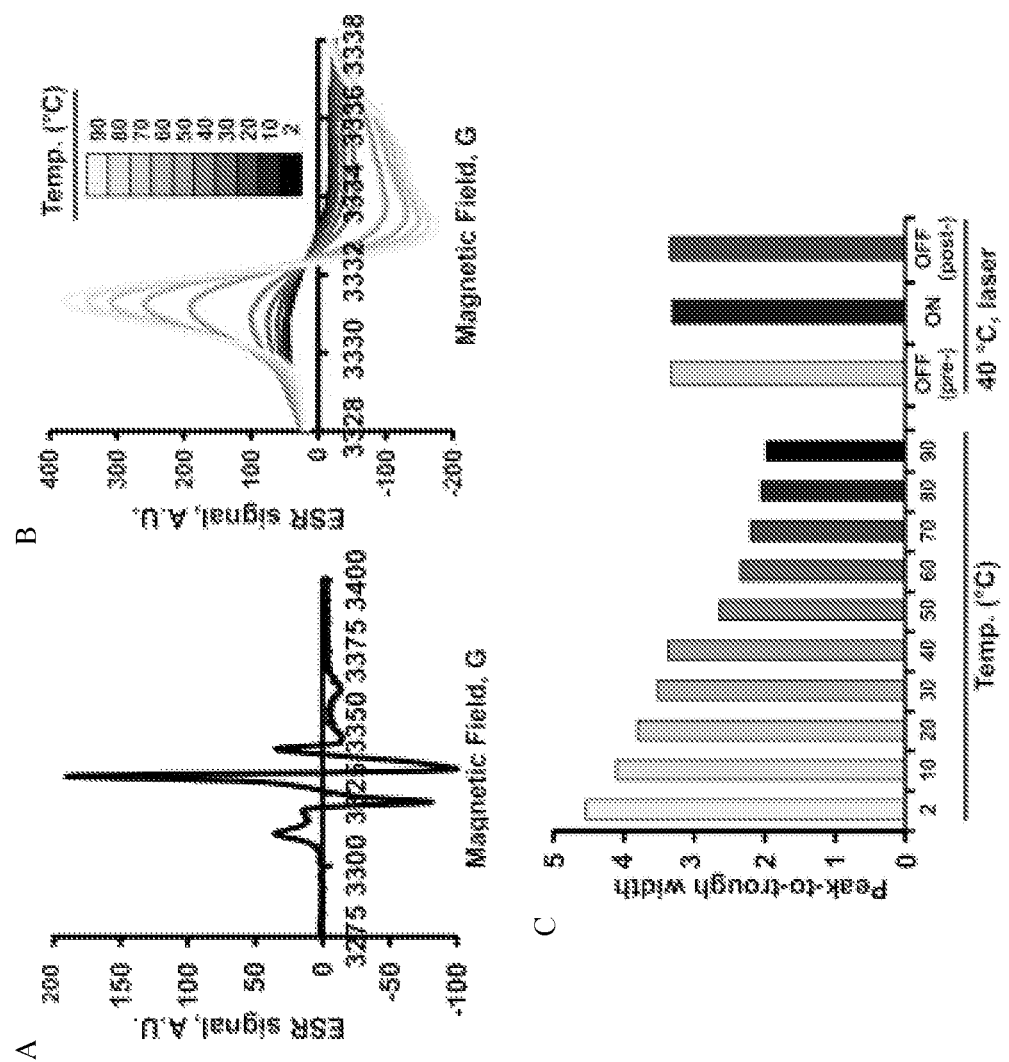

FIG. 11. Demonstration that porphyrin-phospholipid doping enables NIR-mediated liposomal cargo unloading in the absence of bulk or nanoscale heating. a) Electron spin resonance (ESR) of a PoP-liposome sample containing 1 molar % 5-DSA as a spin label, recorded at 50° C. b) Temperature dependence of ESR spectra of 5-DSA containing PoP-liposomes. c) Evidence for lack of nanoscale heating in irradiated PoP-liposomes. The central ESR peak-to-trough width is shown for PoP-liposomes containing 5-doxyl steric acid (5-DSA) at various temperature and before, during and after irradiation that induces permeabilization.

Figure 12:
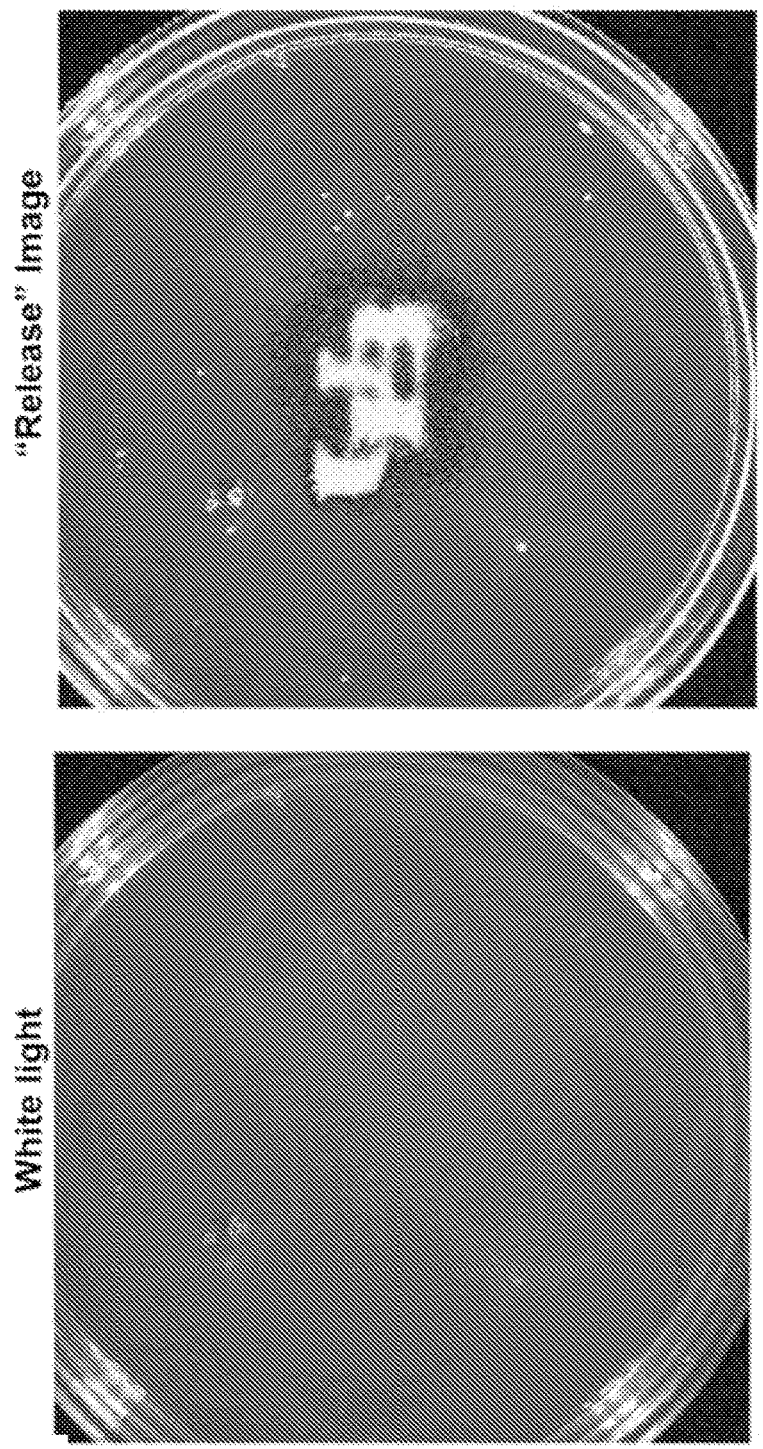

FIG. 12. Demonstration that HPPH phospholipid doping yields thermal and non-exchangeable stability in PoP-liposomes. Sulforhodamine B loaded PoP-liposomes were added to hot agarose (~60 C) prior to pouring and solidification. A laser was used to mediate cargo release with high spatial control and spell "UB". Note the dye is distributed equally everywhere in the agarose.

Figure 13:
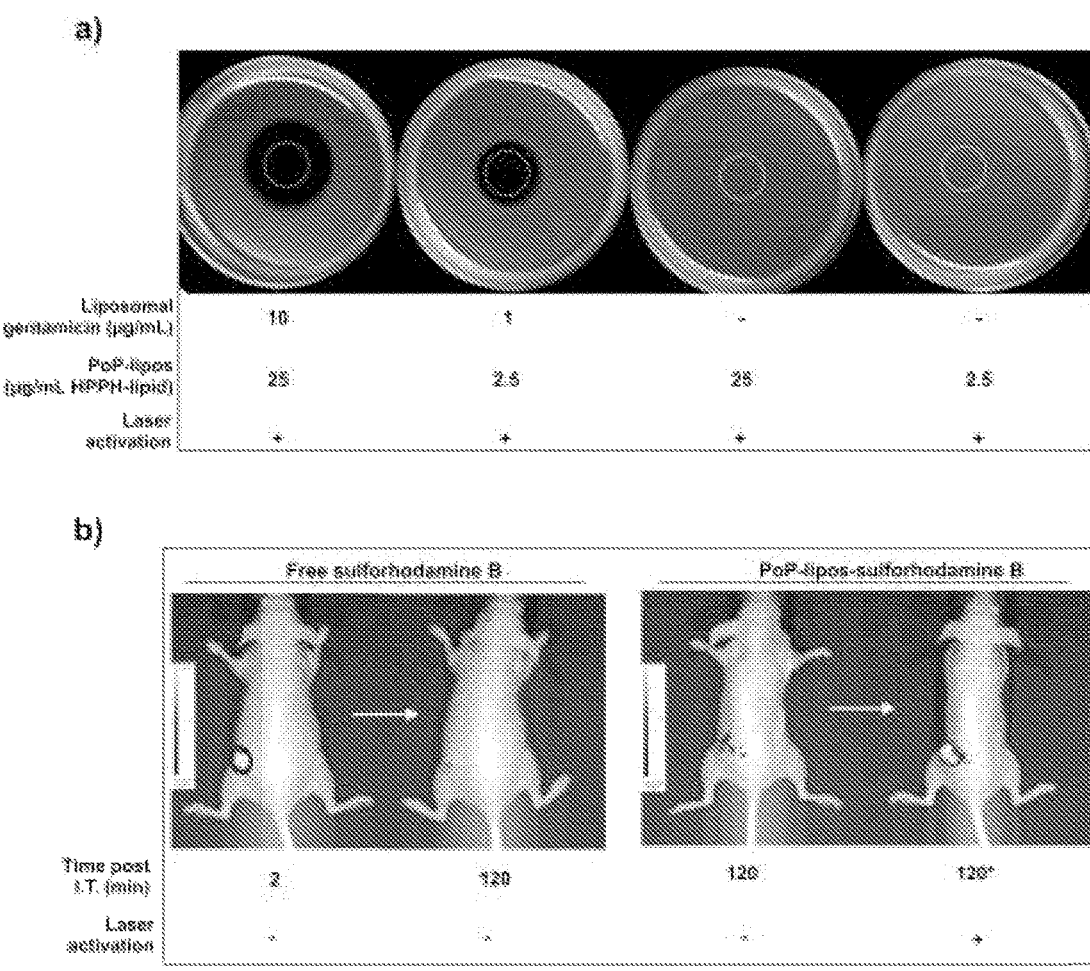

FIG. 13. Example of spatial and temporal control of PoP-liposome permeabilization a) Spatial control of B. subtilis killing with triggered antibiotic release. Gentamicin was loaded in PoP-liposomes and embedded in hot agar along with the bacteria. The indicated spot was irradiated with a 658 nm laser (200 mW/cm$^2$) for 10 minutes and the plates were photographed 24 hours later. b) Temporal control of cargo release in Panc-1 xenografts. Mice were imaged following intratumoral injection of 5 nmol of either free sulforhodamine B or sulforhodamine B entrapped at self-quenching concentrations in PoP-liposomes. Representative images are shown of the indicated time points and conditions. Laser activation was performed after 2 hours. Representative results shown with n=3 mice per treatment group.

Figure 14:
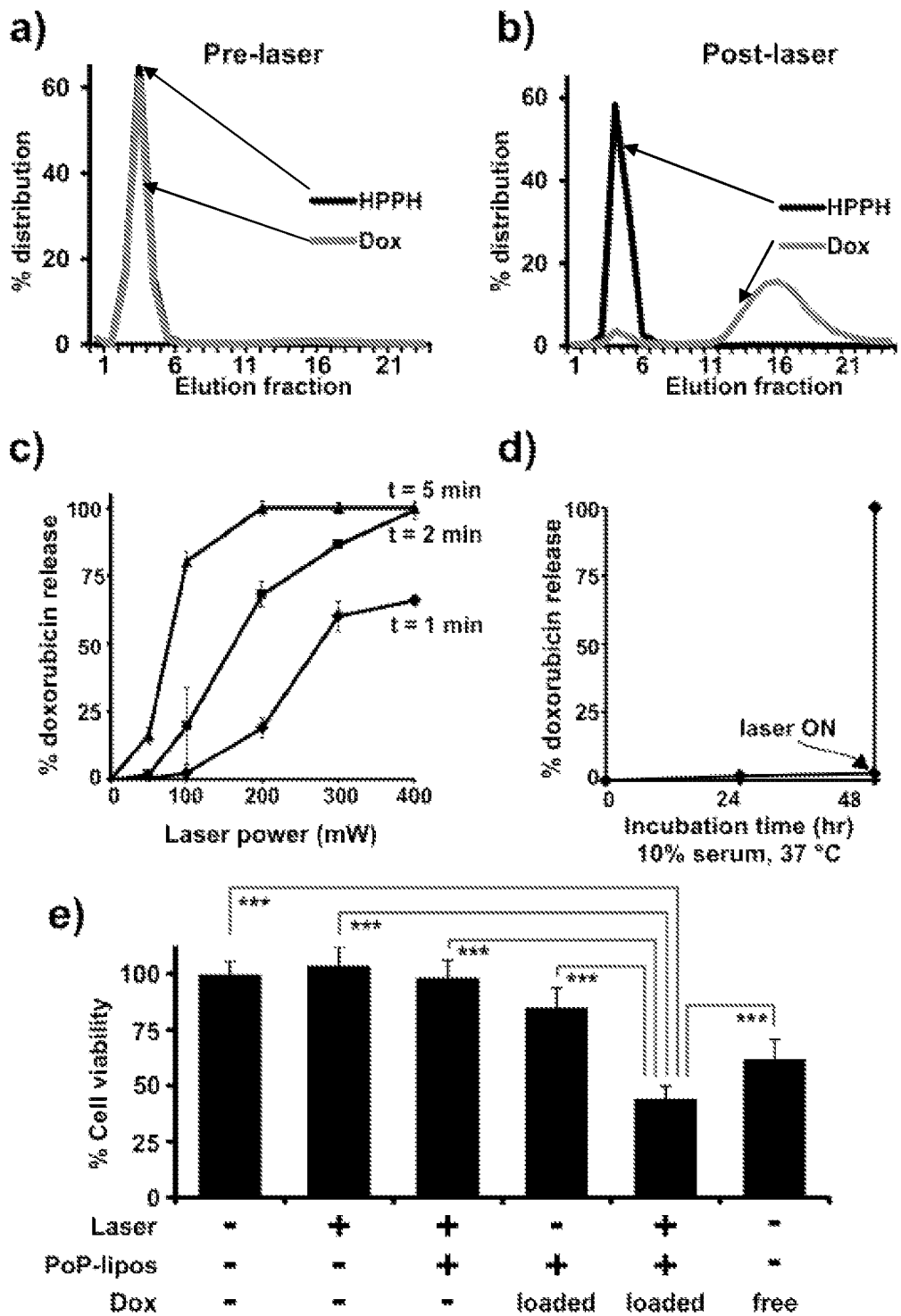

FIG. 14. Example of tunable, on-demand release of an actively loaded drug (doxorubicin) in PoP-liposomes. a) Gel filtration demonstrating active doxorubin loading in PoP-liposomes. Over 95% of the doxorubicin was loaded in dox-PoP-liposomes using a 10:1 lipid to drug ratio at 60° C. for 1 hour. b) Gel filtration of liposomes following laser irradiation showing effective light-triggered release. c) Tunable drug release using PoP-liposomes. Dox-PoP-liposomes were irradiated at varying times and laser powers in media containing 10% serum. Release was assessed using fluorescence. Mean+/−SD (standard deviation) for n=3. d) Stability of dox-PoP-liposomes incubated in 10% serum at 37° C. for two days and subsequently subjected to 4 minute, 300 mW laser irradiation. Mean+/−SD for n=3. e) In vitro cell killing using dox-PoP-liposomes. Panc-1 cells were incubated as indicated for 24 hours with 10 μg/mL doxorubicin following exposure to 200 mW/cm$^2$ irradiation for 10 minutes. After 24 hours, the media was replaced and viability was assessed 24 hours later using the XTT assay. Mean+/−SD for n=8. ***Laser+dox-PoP-liposomes induced significant inhibition of cell viability compared to all other groups based on one-way analysis of variance with post-hoc Tukey's test (P<0.001).

Figure 15:
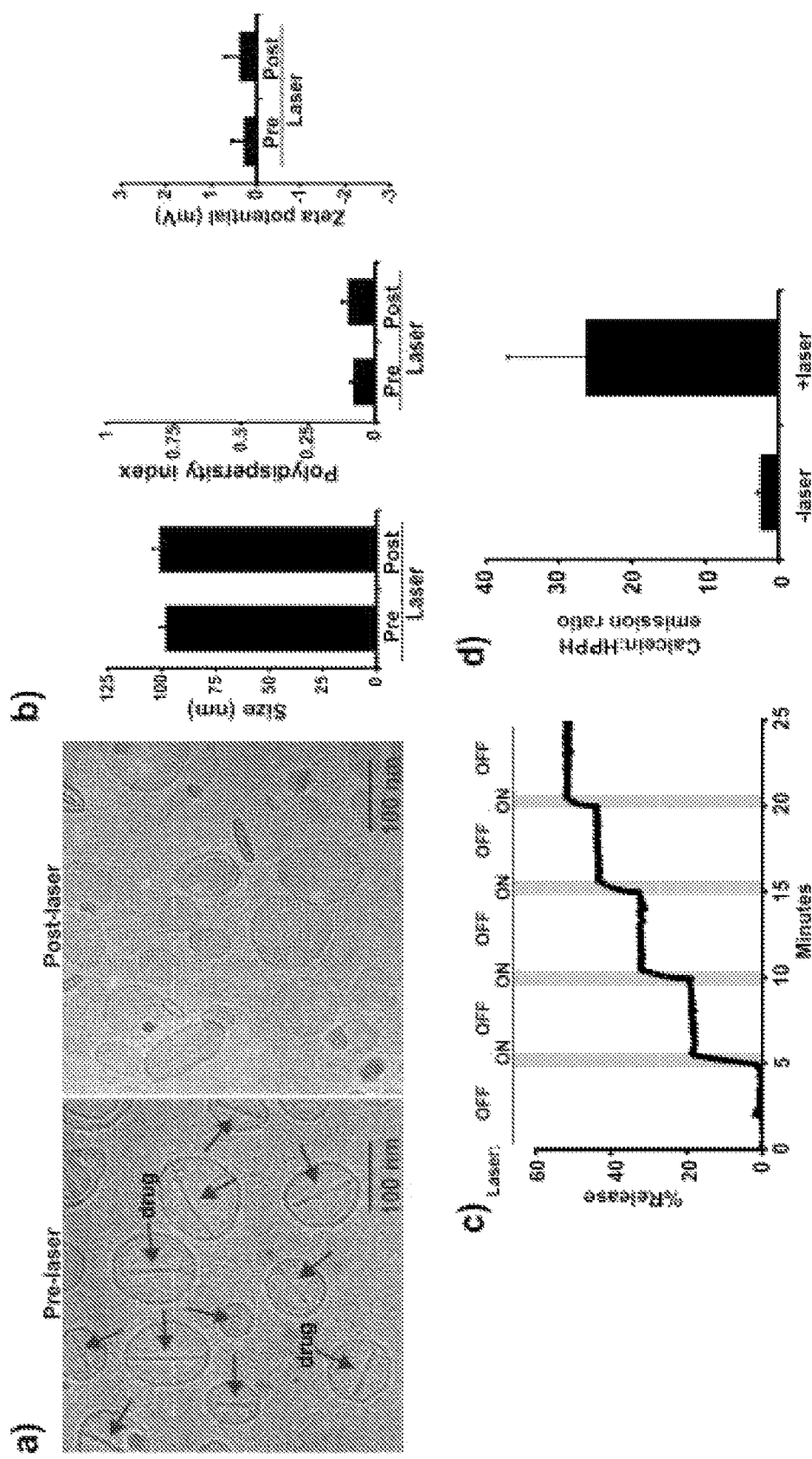

FIG. 15. Representative a) cryo-TEM images of dox-PoP-liposomes before and after irradiation. Arrows indicate the formation of doxorubicin-sulfate aggregates within the liposomes. b) Dynamic light scattering size, polydispersity index and zeta potential before and after laser-induced release of dox-PoP-liposomes c) Temporary induced permeability as demonstrated by periodic laser irradiation of calcein-loaded PoP liposomes. d) Empty PoP-liposomes were incubated in a 2 mM calcein solution and irradiated with 120 mW laser irradiation for 3 minutes. Free calcein and PoP-liposome-entrapped calcein were separated with gel filtration and the ratio of calcein emission to HPPH emission (using separate excitation and emission settings) was measured. Mean+/−SD for n=3.

Figure 16:
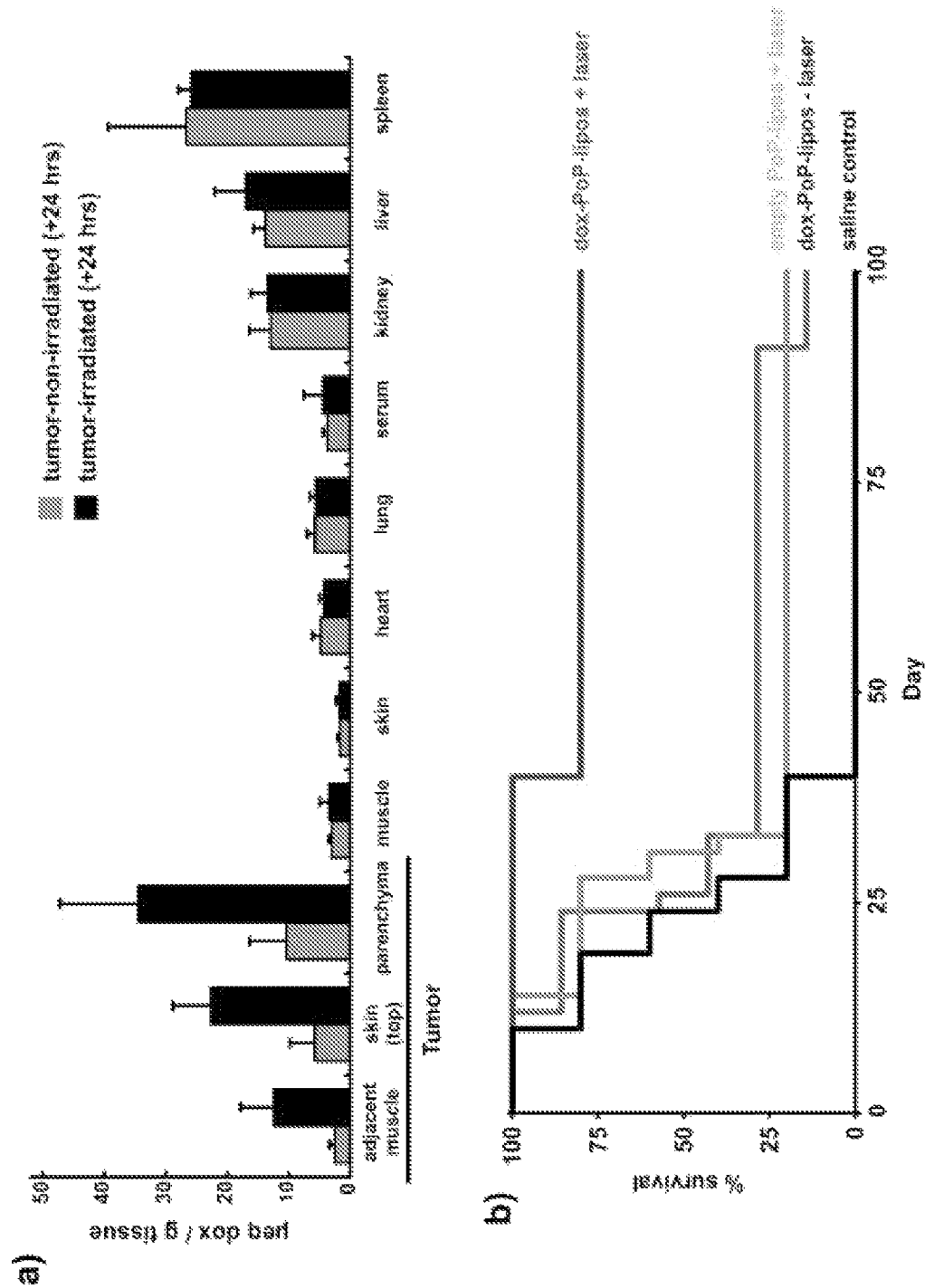

FIG. 16. Example of Dox-PoP-liposomes as a systemically-administered, single-treatment anti-tumor phototherapy. a) Biodistribution of doxorubicin+/−laser treatment. Nude mice bearing KB tumors were I.V. injected with dox-PoP-liposomes (10 mg/kg dox) and 15 minutes later, the tumor was irradiated with a 658 nm laser at 200 mW/cm$^2$ fluence rate for 12.5 minutes (150 J/cm$^2$). Mean+/−SD for n=7-8 mice per group. b) Kaplan-Meier survival curve for nude mice bearing KB tumors. Mice were given a single treatment when tumors reached 4-6 mm and were sacrificed when tumors reached 10 mm in any direction. Mice were treated with dox-PoP-liposomes (10 mg/kg dox) as above or a corresponding amount of empty PoP-liposomes. n=5-7 mice per group.

Figure 17:
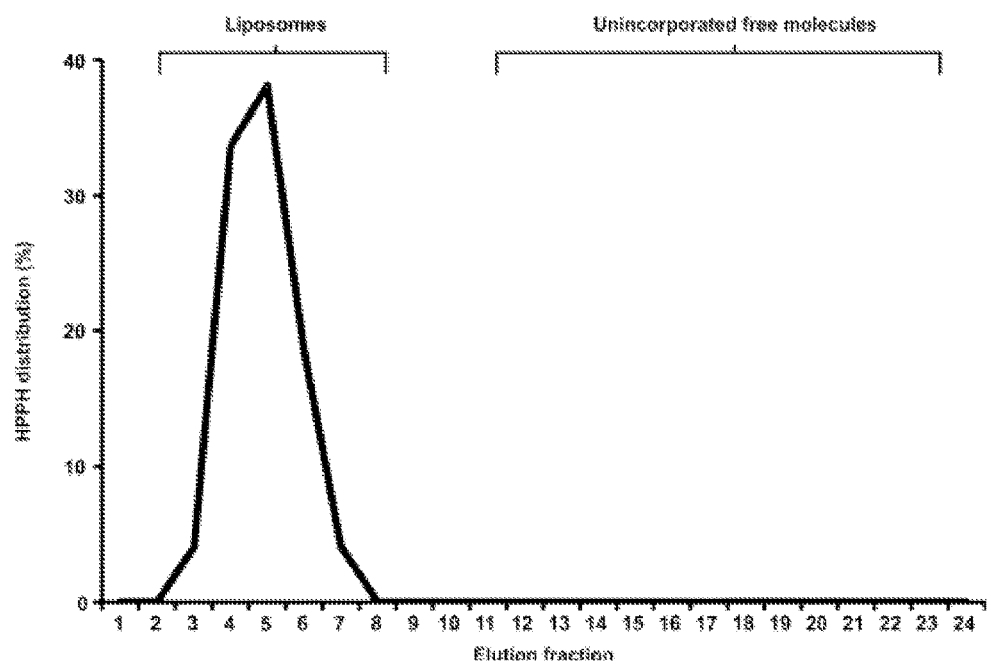

FIG. 17. Representative effective loading of 10 molar % free HPPH into liposomes. Liposomes containing 50 mol. % DSPC, 35 mol. % cholesterol, 5 mol. % DSPE-PEG2K and 10% free HPPH were formed from the thin film method, hydrated with buffered saline, sonicated and subjected to gel filtration. The elution fractions of liposomes and free molecules are indicated. All samples were lysed with 0.25% Triton-X100 prior to fluorescence measurement of HPPH.

Figure 18:
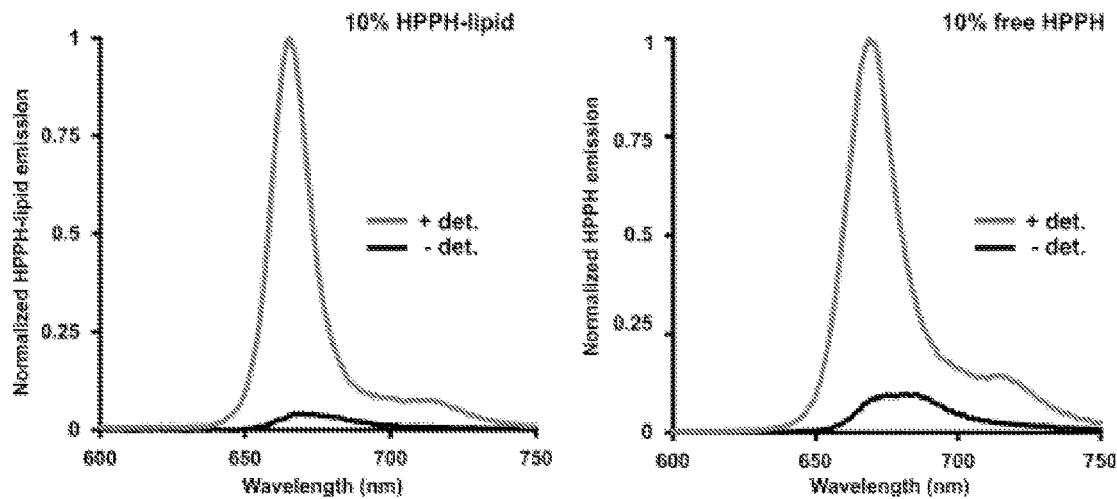

FIG. 18. Representative fluorescence self-quenching of PoP-liposomes containing 10 molar % HPPH phospholipid or 10 molar % free HPPH. Liposomes were formed with 50 mol. % DSPC, 35 mol. % cholesterol, 5 mol. % DSPE-PEG2K, and 10 mol. % either free HPPH or HPPH phospolipid. Liposomes formed with 10% HPPH phospholipid exhibited HPPH fluorescence quenching of 97% (~30 fold) whereas liposomes containing 10% free HPPH were quenched 92% (~13 fold). Samples were measured in PBS and 0.25% Triton-X100 was used to lyse the liposomes.

Figure 19:
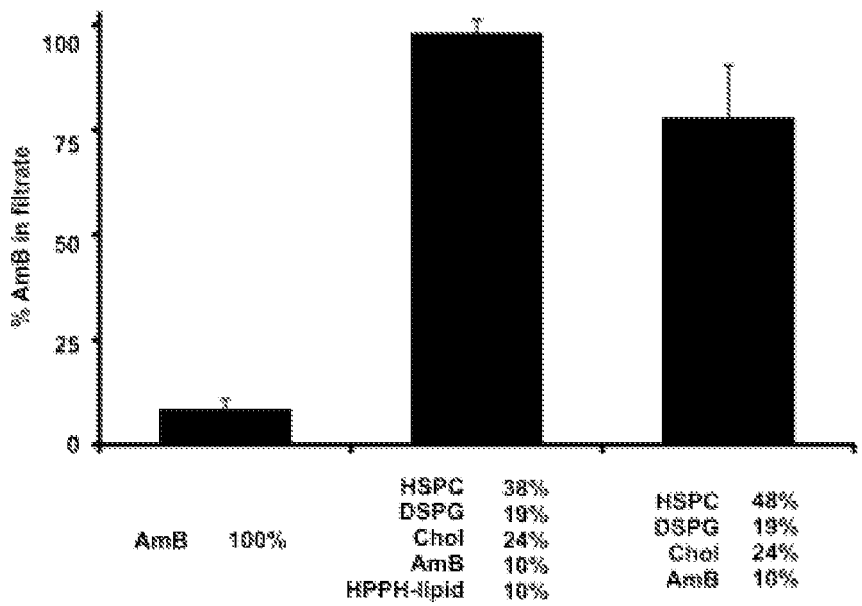

FIG. 19. Demonstration of that HPPH phospolipid does not interfere with Amphotericin B loading in membranes. Amphotericin B (AmB) was loaded into liposomes composed of the indicated lipids or free amphotericin B via thin film hydration of 10 mg films. The samples were sonicated and filtered and the resulting amphotericin B in percentage of soluble AmB that could enter the filtrate was assessed via fluorescence (mean+/−SD for n=3).

Figure 20:
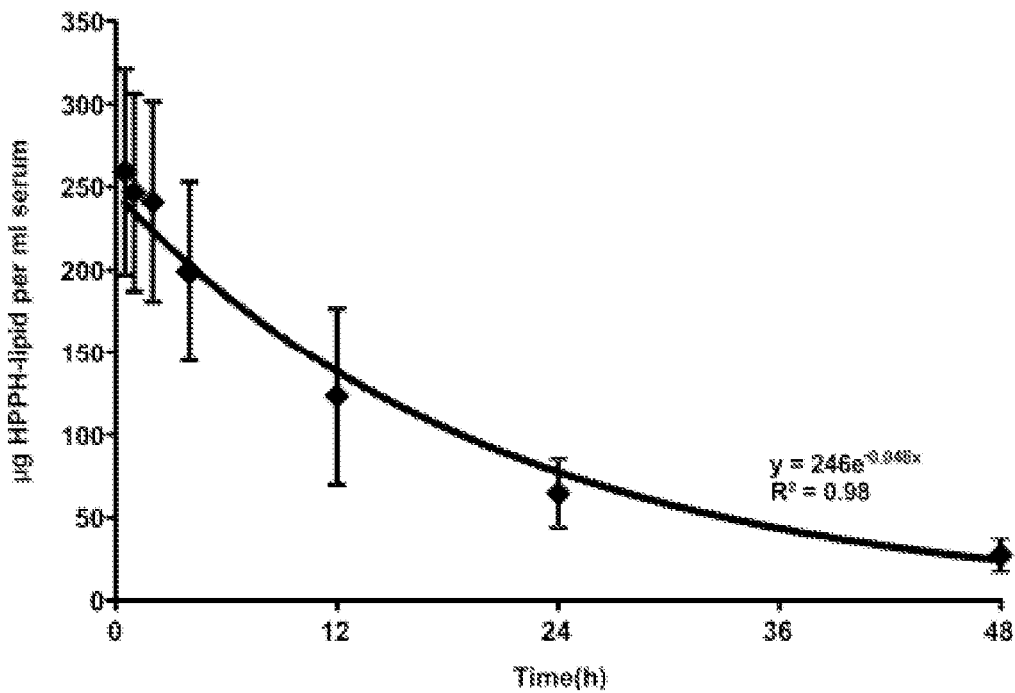

FIG. 20. Example of half-life of PoP-liposomes in mice following intravenous injection. PoP-liposomes (composed of 50 mol. % DPSC, 35 mol. % cholesterol, 10 mol. % HPPH phospholipid and 5 mol. % DSPE-PEG2K) were injected via tail vein into BALB/c mice (15 mg/kg based on HPPH phospholipid). Serum was sampled and HPPH phospolipid was detected using fluorescence. A single compartment circulating half-life of 14.4 hrs was observed (SD of 1.4 hours for n=5 mice).

Figure 21:
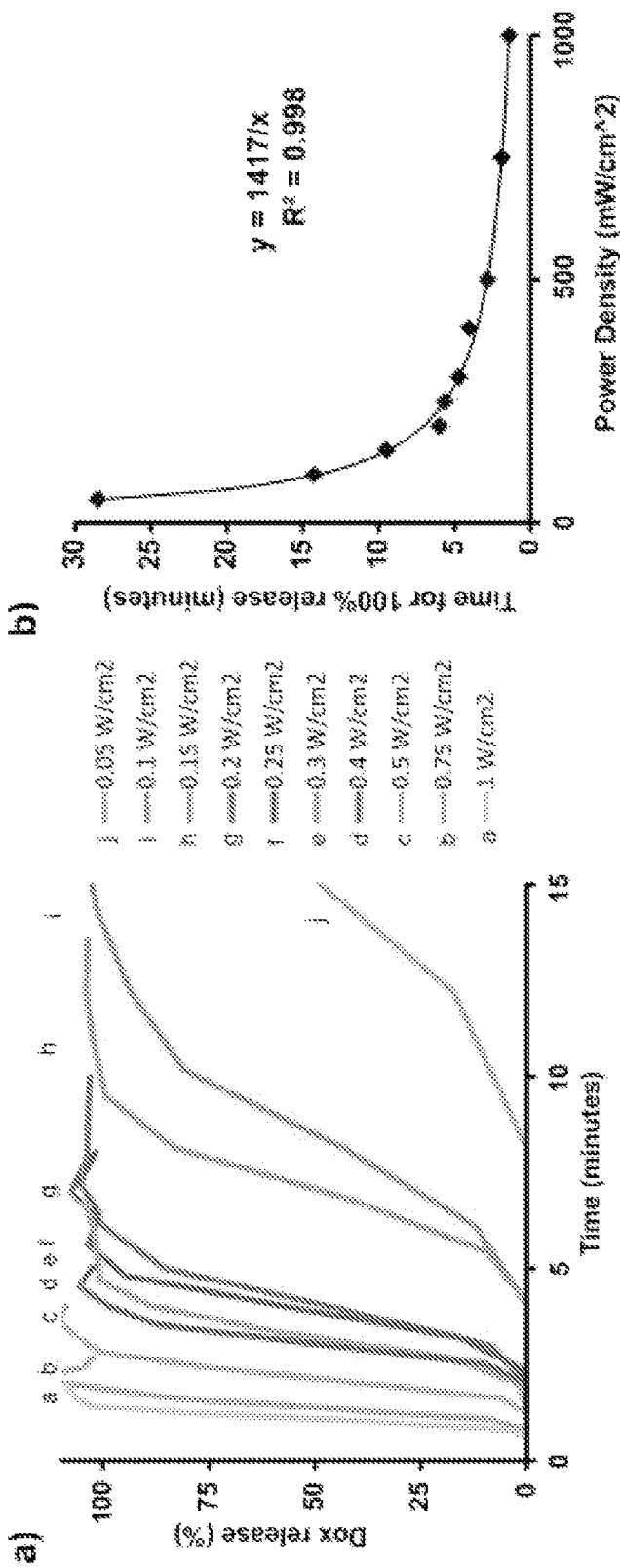

FIG. 21. Example of release of doxorubicin depends only on total fluence, regardless of fluence rate. a) Doxorubicin release from PoP-liposomes as a function of time. b) Time required for 100% doxorubicin release at different power densities.

Figure 22:
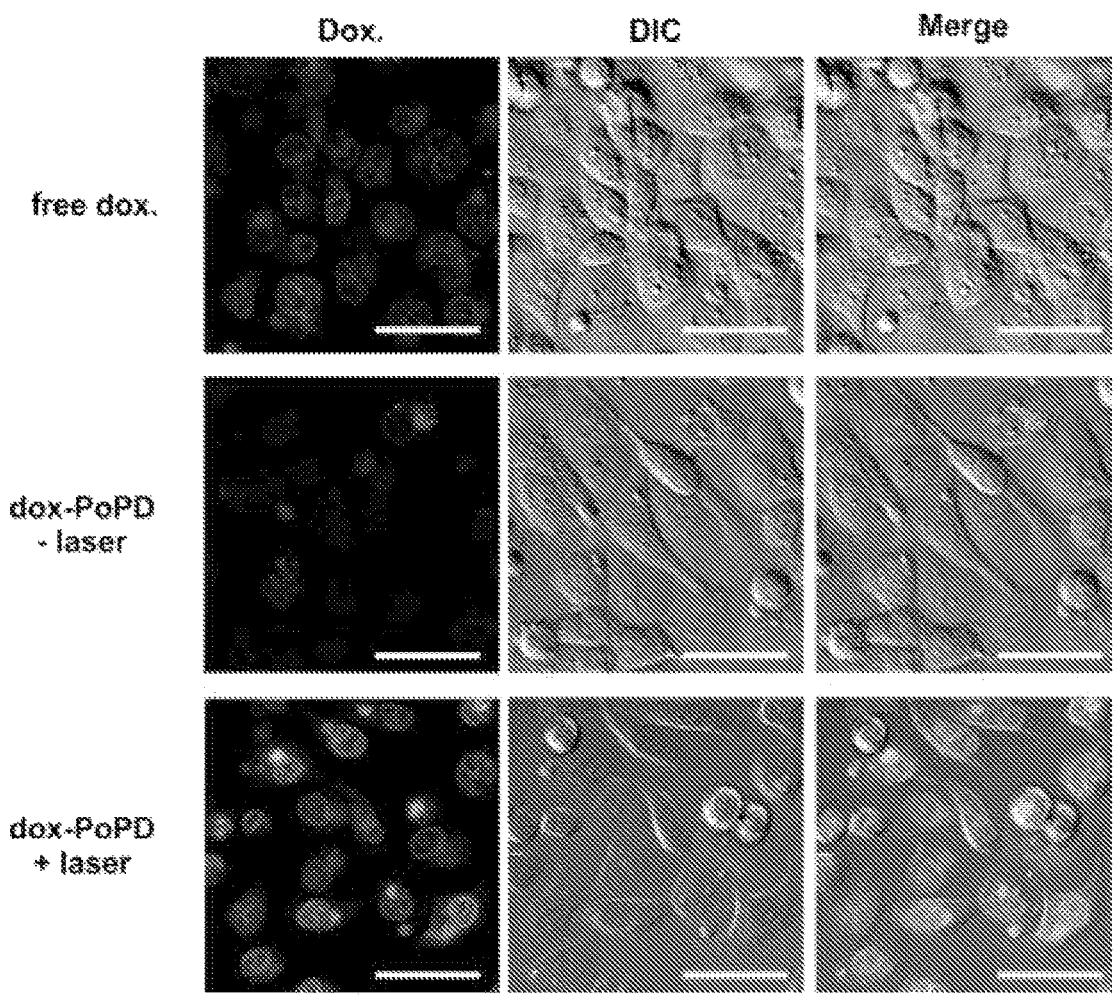

FIG. 22. Example of doxorubicin release from PoP-liposomes in Panc-1 cells. Panc-1 cells were seeded in chamber slides and incubated for 3 hours in 10% serum with 10 μg/mL doxorubicin in either free or PoP-liposomal form prior to confocal imaging. Laser treatment occurred at the beginning of the incubation period (658 nm, 200 mW/cm$^2$, 5 minute treatment). 50 μm scale bar is shown.

DESCRIPTION OF THE DISCLOSURE

In this disclosure, provided is a controlled-release nanosystem using porphyrin-phospholipid nanovesicles (PoP-NVs). Release of cargo from the PoP-NVs can be triggered directly by near infrared (NIR) light, a clinically-applicable stimulus that has negligible actuation in the "off state" and minimal interference with surrounding biological tissues.

The present disclosure is based on the surprising observation that a structural modification to porphyrin-phospholipid compounds imparted both 1) stable loading and 2) controlled- release properties to nanovesicles prepared from the compounds. The PoP-NVs of the present disclosure provide a stable bilayer and display cargo retention even at 90° C. However, rapid and controlled release was induced upon exposure to mild NIR irradiation. Remarkably, release occurred in the absence of any bulk solution photothermal heating or chemical reactions. Induced permeability can be used for both loading and unloading cargo and could be modulated by varying porphyrin doping or laser irradiation intensity and duration.

In one aspect, the present disclosure provides nanovesicles and compositions comprising nanovesicles. The bilayer of the nanovesicles comprises porphyrin conjugates. The porphyrin conjugate making up some or all of the bilayer of the nanovesicles comprises porphyrins, porphyrin derivatives, porphyrin analogs, or combinations thereof. Exemplary porphyrins include hematoporphyrin, protoporphyrin, and tetraphenylporphyrin. Exemplary porphyrin derivatives include pyropheophorbides, bacteriochlorophylls, Chlorophyll A, benzoporphyrin derivatives, tetrahydroxyphenyl chlorins, purpurins, benzochlorins, naphthochlorins, verdins, rhodins, keto chlorins, azachlorins, bacteriochlorins, tolyporphyrins, and benzobacteriochlorins. Exemplary porphyrin analogs include expanded porphyrin family members (such as texaphyrins, sapphyrins and hexaphyrins) and porphyrin isomers (such as porphycenes, inverted porphyrins, phthalocyanines, and naphthalocyanines).

In certain embodiments, the porphyrin conjugate comprises a metal chelated therein, preferably a divalent metal such as Zn, Cu, Ni, Co, Pd or Mn, and optionally a radioisotope of a metal such as Cu-64.

As used herein, "phospholipid" is a lipid having a hydrophilic head group having a phosphate group connected via a glycerol backbone to a hydrophobic lipid tail. The phospholipid comprises an acyl side chain of 6 to 22 carbons, including all integer number of carbons and ranges therebetween. In certain embodiments, the phospholipid in the porphyrin conjugate is 1-palmitoyl-2-hydroxy-sn-glycero-3-phosphocholine.

The phospholipid in the porphyrin conjugate may comprise, or consist essentially of phosphatidylcholine, phosphatidylethanoloamine, phosphatidylserine and/or phosphatidylinositol.

In one embodiments, the porphyrin in the porphyrin conjugate is Pyropheophorbide-a hexyl ether (HPPH).

In certain embodiments, the porphyrin is conjugated to the glycerol group on the phospholipid by a carbon chain linker of 1 to 20 carbons, including all integer number of carbons therebetween.

Without intending to be bound by any particular theory, it is considered that the ether sidechain of the porphyrin conjugate provides the nanovesicle with improved bilayer density. The alkyl ether side-chain can contain from 2 to 20 carbons, including all integer number of carbons and ranges therebetween. The alkyl portion of the ether side-chain can be linear or branched.

In certain embodiments, the bilayer of the self-assembled nanovesicle further comprises PEG or PEG-lipid. The PEG or PEG-lipid can be DSPE-PEG such as DSPE-PEG-2000, DSPE-PEG-5000 or other sizes of DSPE-PEG. The PEG-lipid is present in an amount of 0-15 mol. % including all integers therebetween. In certain embodiments it is 1 to 15 mol. %, 2 to 10 mol. %, 4 to 6 mol. %. In one embodiment, it is 5 mol. %.

In various embodiments, in addition to the porphyrin conjugates disclosed herein, the bilayer of the nanovesicles also comprises other phospholipids. The fatty acid chains of these phospholipids may contain a suitable number of carbon atoms to form bilayer. For example, the fatty acid chain may contain 12, 14, 16, 18 or 20 carbon atoms. In different embodiments the bilayer may comprise phosphatidylcholine, phosphatidylethanoloamine, phosphatidylserine and/or phosphatidylinositol.

In various embodiments, the nanovesicles may include lipids or phospholipids covalently modified with polyethylene glycol (PEG). This PEG-lipid may be present from 0.1 to 20 mol. % and all values to the tenth decimal place therebetween and ranges therebetween in the nanovesicles. The average molecular weight of the PEG moiety can be between 500 and 5000 Daltons and all integer values and ranges therebetween.

In one embodiment, the nanovesicles are cholesterol-free. In other embodiments, cholesterol can be from 0.1 to 60 mol. % and all values to the tenth decimal place therebetween and ranges therebetween. In an embodiment, the cholesterol is in the bilayer. The use of the PoP-NV monomer of the present disclosure enabled effective loading of cargo into serum-free, cholesterol-free nanovesicles and use of mild NIR resulted in rapid and up to 100% release of cargo.

The present disclosure provides a porphyrin phospholipid conjugate having the following structure:

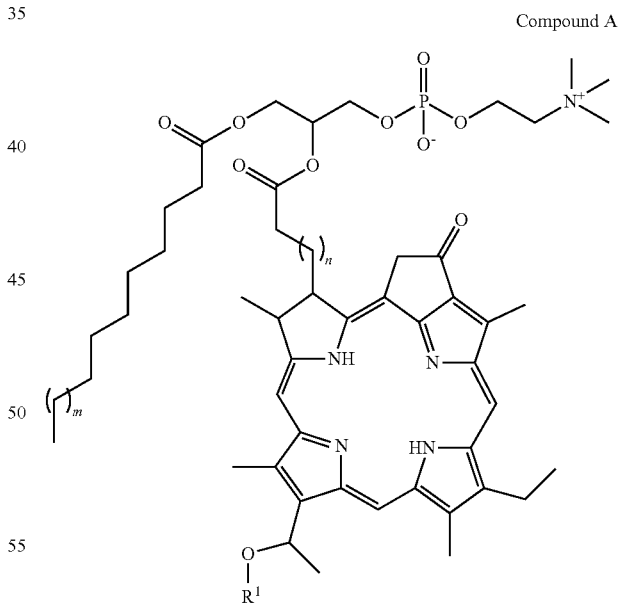

Compound A

This compound is referred to herein as Compound A, where m is an integer from 1 to 12, n is an integer from 1 to 12, and $R^1$ is a hydrogen atom, a branched or liner alkyl group having from 2 to 20 carbon atoms. In an embodiment, $R^1$ is not a hydrogen atom.

In one embodiment, the present disclosure provides a porphyrin conjugate having the following structure—referred to herein as PC-HPPH-C16 or Compound B (also referred to herein as 16-HPPH-C16).

Compound B

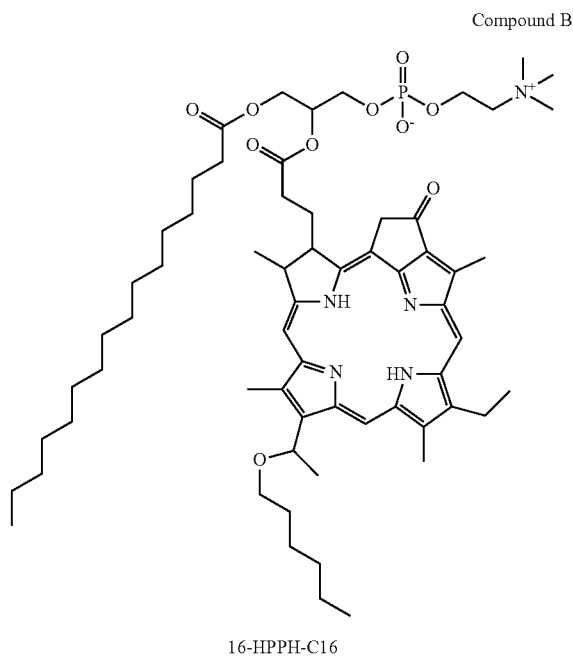 [SMILES: CCCCCCCCCCCCCCCC(=O)OCC(COP(=O)([O-])OCC[N+](C)(C)C)OC(=O)CCC1c2[nH]c(cc3nc(cc4[nH]c(cc5nc6c2CC(=O)C6=C5C)c(CC)c4C)C(C(C)OCCCCCC)=C3C)C1C]

16-HPPH-C16

Compound C

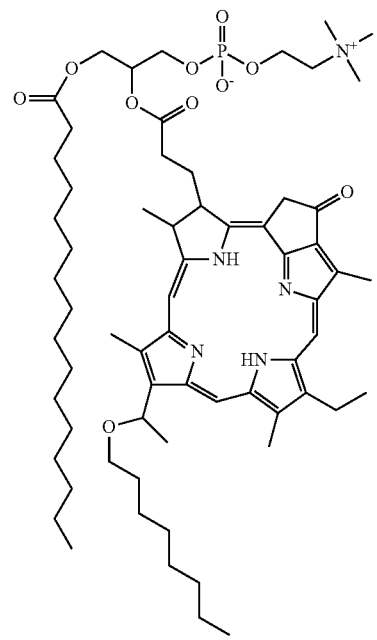

In one embodiment, the nanovesicle comprises a bilayer comprising porphyrin conjugate comprising a porphyrin and a phospholipid, the porphyrin has an alkyl ether sidechain. In one embodiment, the nanovesicle comprises a bilayer comprising a porphyrin conjugate having the structure of Compound A. In another embodiment is provided a nanovesicle comprising a bilayer comprising a porphyrin conjugate having the structure of PC-HPPH-C16.

In various embodiments, the present disclosure provides a porphyrin conjugate having one of the following structures:

Compound B

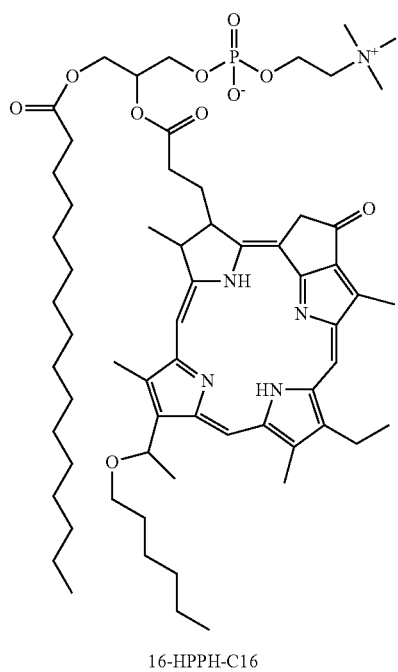

16-HPPH-C16

Compound D

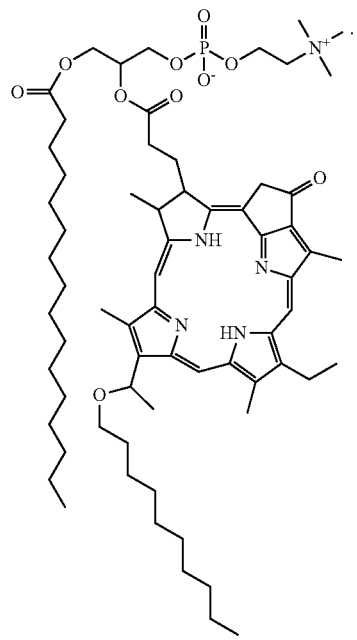

The bilayer of the nanovesicle of the present disclosure can comprise from 1 to 100 mol. % of the porphyrin phospholipid conjugate compounds of the present disclosure. In various embodiments, the nanovesicle bilayer is comprised of at least 5, 10, 15, 25, 35, 45, 55, 65, 75, 85, 95 mol. % (and all integers there between) porphyrin phospholipid conjugate. In contrast to the requirement of at least 15 mol. % disclosed in US Patent Publication No. 2012/0253191, it was unexpectedly observed that the mol. % of the porphyrin phospholipid conjugate compounds of the present disclosure could be less than 15% to achieve effective light-triggered release. Thus, in one embodiment, the PoP-NV is made up of less than 15 mol. % porphyrin phospholipid conjugate. In another embodiment, the nanovesicle bilayer comprises from 0.1 to 14.4 mol. %, 5 to 14 mol. %, porphyrin phospholipid conjugate and all values to the 0.1 mol. % and ranges therebetween. In other embodiments, the nanovesicle bilayer comprises 1, 2, 3, 4, 5, 6, 7, 8, 9, 10, 11, 12, 13 or 14 mol. % of the porphyrin phospholipid conjugate. In one embodiment, the nanovesicle bilayer comprises 9.5 to 10.5 mol. % porphyrin phospholipid conjugate. The doping level should be such as to confer light-triggered release of loaded cargo. In another embodiment, the PoP-NV bilayer is made up of more than 15 mol. % porphyrin phospholipid conjugate, or between 15-100% porphyrin phospholipid conjugate, provided that the porphyrin-phospholipid monomer confers both stable cargo loading in the absence of NIR irradiation and cargo release upon NIR exposure.

The nanovesicles are substantially spherical and have a size of from 30 nm at 250 nm in diameter and all integer to the nm and ranges therebetween. In one embodiment, the size of the nanovesicles is from 100-175 nm. In one embodiment, at least 50%, 60%, 70%, 80%, 85%, 90%, 95%, 99%, or 100% of the nanovesicles in the composition have a size of from 30 to 250 nm or from 100 to 175 nm.

In one aspect, the disclosure provides a composition comprising nanovesicles of the present disclosure and a sterile, suitable carrier for administration to individuals including humans—such as a physiological buffer such as sucrose, dextrose, saline, pH buffering (such as from pH 5 to 9, from pH 7 to 8, from pH 7.2 to 7.6, (e.g., 7.4)) element such as histidine, citrate, or phosphate. In one embodiment, the composition comprises at least 0.1% (w/v) PoP-NVs of the present disclosure. In various embodiments, the composition comprises from 0.1 to 100% PoP-NVs. In one embodiment, a part of the agent molecule (cargo) may be embedded in the bilayer. An example of hydrophobic cargo loaded into the bilayer is Amphotericin B.

A wide variety of cargo may be loaded into the nanovesicles of the present disclosure and delivered to desired locations using near infrared light. For example, bioactive or therapeutic agents, pharmaceutical substances, or drugs can be encapsulated within the interior of the PoP-NV. This includes water soluble drugs and also drugs that are weak acids or bases that can be loaded via chemical gradients and concentrated in the aqueous core of the nanovesicle. Thus, in various embodiments, the nanovesicle comprises an active agent encapsulated therein, such as a therapeutic agent or a diagnostic agent, which can be a chemotherapy agent such as doxorubicin. The chemotherapeutic agent doxorubicin could be actively loaded and released with NIR irradiation providing for robust and direct light-triggered release using PoP nanovesicles.

In one embodiment, the ratio of lipid to drug (or any other cargo agent) ratio is from 10:1 to 5:1. In various embodiments, the ratio of lipid to drug/cargo ratio is 10:1, 9:1, 8:1, 7:1, 6:1, or 5:1.

The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Drugs that are known to be loaded via active gradients include doxorubicin, daunorubicin, gemcitabine, epirubicin, topotecan, vincristine, mitoxantrone, ciprofloxacin and cisplatin. Therapeutic cargo also includes various antibiotics (such as gentamicin) or other agents effective against infections caused by bacteria, fungi, parasites, or other organisms. These drugs can be loaded and released in PoP-NVs.

A "diagnostic" or "diagnostic agent" is any chemical moiety that may be used for diagnosis. For example, diagnostic agents include imaging agents, such as those containing radioisotopes such as indium or technetium; contrasting agents containing iodine or gadolinium;

enzymes such as horse radish peroxidase, GFP, alkaline phosphatase, or .beta.-galactosidase; fluorescent substances such as europium derivatives; luminescent substances such as N-methylacrydium derivatives or the like.

In certain embodiments, the nanovesicle further comprises targeting molecule, such as an antibody, peptide, aptamer or folic acid. "Targeting molecule" is any molecule that can direct the nanovesicle to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, or single chain, many of which are commercially available or readily obtained using standard techniques.

In one aspect, the disclosure provides a method of preparing a nanovesicle comprising mixing a porphyrin-phospholipid conjugate in buffer, wherein the porphyrin-phospholipid conjugates are as described herein, and extruding the mixture to yield a porphyrin-phospholipid bilayer nanovesicle comprising a bilayer of the desired amount of the porphyrin-phospholipid conjugate. In addition to the porphyrin-phospholipid, other phospholipids or lipids may be included in the mixture to make the PoP-NVs. For example, in one embodiment, DSPE-PEG-2K (e.g. 5 mol %); cholesterol (e.g. 35 mol %) and lipid (e.g. DSPC 50 mol %) may be used. Propyrin-phospholipid conjugate may be prepared by esterifying a carboxylic acid-bearing tetrapyrrole to a lyso-phospholipid. For example, HPPH can be esterified at room temperature with 1-palmitoyl-2-hydroxy-sn-glycero-3-phosphocholine (lyso-C16-PC), Avanti #855675P) using EDC and 4-dimethylaminopyridine (DMAP, Disher #AC14827-0250) in chloroform at a 1:1:2:2 lyso-C16-PC|HPPH:EDC:DMAP molar ratio.

In one embodiment, PoP-NVs are formed by dispersing porphyrin-lipid, PEG-lipid, cholesterol and other lipid components in chloroform then evaporating the solvent. The lipid film is hydrated with a buffer (such as phosphate buffered saline (PBS)) and then, following freeze thaw cycles, PoP-NVs are extruded through a filter membrane (such as a 100 nm polycarbonate membrane) multiple times. Alternatively, or additionally, high pressure lipid extruder can also be used. For fluorophore-loaded PoP-NVs, the hydrating solution is typically calcein (100 mM). Free calcein can be removed by gel filtration (such as with a Sephadex PD-10 column). For active drug loading, as an example, a hydrating solution of 125 mM ammonium sulfate, pH 5.5, can be used. Free ammonium sulfate can be removed by gel filtration or dialysis and the active agent can be actively loaded into the PoP-NVs using, for example, a 10:1 lipid:drug ratio. Loading efficacy and entrapment of both calcein and active agents can be assessed by examing the included and excluded gel filtration fractions. Altenatively, for certain cargo, loading can be monitored using a fluorescence reader, comparing the fluorescence of the PoP-NV sample to the initially loaded PoP-NVs as well as PoP-NVs permeabilized with Triton X-100 detergent (such as 0.5%). Calcein and active agent (such as doxorubicin) can be detected by appropriate excitation and emission wavelengths. For example, 485 nm excitation and 525 nm emission can be used for the calcein and 480 nm excitation and 590 nm emission is used to detect active agent such as doxorubicin. PoP-NV self-assembly status and elution position can also tracked without interference by using 420 nm excitation and 670 nm emission for porphyrins.

In one aspect, the disclosure provides a method of delivery of agents contained as cargo in the nanovesicles to desired locations. Although at times, cargo is described as drug in the disclosure, the description is equally applicable to any agent contained for treatment and/or delivery to a desired location, and the term "drug" is intended to refer to any agent. The agent may be contained, in whole or in part, within or in the PoP-NVs—whether present in the aqueous compartment, the bilyer or both. Thus, in another aspect, the disclosure provides a method for delivery of cargo of a nanovesicle comprising the steps of: 1) providing a composition comprising nanovesicles of the present disclosure comprising the cargo (such as an active agent); 2) allowing the nanovesicles to reach a selected or desired destination; 3) irradiating the nanovesicle with radiation having a wavelength of near-infrared under conditions such that at least a portion of the cargo is released from the nanovesicle.

The method of the present disclosure can be carried out in vitro or in vivo. When carried out in vivo, in one embodiment, the irradiation with near-infrared radiation is such that the temperature of the surrounding tissue does not increase more than 10 degrees Celsius. In various embodiments, the temperature of the surrounding tissue does not increase more than 5, 6, 7, 8, 9 and 10, 11 and 12 degree Celsius. In other embodiments, the temperature of surrounding tissue increases by less than 5 degrees Celsius. The method of the present disclosure can be used in any individual of any age including animals and humans.

The nanovesicles are irradiated with near-infrared light from a laser of power 50 to 1000 mW/cm$^2$, including all integer values to the mW/cm$^2$ and ranges therebetween, at a wavelength of from 650 to 1000 nm, including all integer values to the nm and ranges therebetween. In another embodiment, the wavelength is from 650 to 800 nm, including all integer values to the nm and all ranges therebetween.

The extent of release of cargo is also dependent upon the exposure time. Generally, a time of up to 30 minutes or less is sufficient. In various embodiments, the nanovesicles in vitro or in vivo may be irradiated from 0.5 to 30 minutes and all values to the tenth decimal place therebetween. In one embodiment, the nanovesicles are irradiated with a 658 nm laser diode for up to 10 minutes. In other embodiments, the nanovesicles are irradiated with wavelengths of 665 or 671 nm. By varying the laser power and/or the laser time, control over how much drug is released from the PoP-NVs is achieved. Further, controlled irradiation to achieve a "small-vessel-only" light-release strategy that can result in lower systemic drug release and will not harm critical vessels in organs with extensive vasculature (such as the pancreas). The infrared radiation can be delivered to the desired area directly by shining laser light on the area or fiber optic probes may be used. In the case of a tumor, the fiber optic probe can be inserted into the tumor (i.e., via a catheter or endoscopic device) to provide irradiation to a localized area. Following laser exposure, the nanovesicles may be resealed. In this manner, the opening and closing of the nanovesicles is reversible. Resealing enables new applications such as capturing contents of tumor vasculature containing tumor-specific small molecules and larger molecules like proteins. This could enable downstream analysis of tumor contents. Also, resealing prevents aggregation so the liposomes may effectively deposit their cargo. Additionally, retrieval of the re-sealed nanovesicles by blood draw or biopsy could be accomplished for assessing treatment progress.

A useful property of the nanovesicles of the present disclosure is there is minimal release (i.e., less than 1% release of contents per hour) of the active agent until near-infrared light is shined at the nanovesicle. In one embodiment, 100% of the active agent (cargo) that is irradiated in the target tissue with sufficient laser power is released from the nanovesicle. When the active agent is released in vivo from the nanovesicle, the temperature of the surrounding tissue does not increase significantly. By selecting the intensity of the NIR applied, the amount of cargo released at a given location or given time can be controlled. Thus, anywhere between 1 to 100% (and all integers therebetween) of the cargo from nanovesicles can be released at desired locations and times. In one embodiment, the release of cargo (anywhere from 1 to 100% of the cargo) is achieved in one or more steps. For example, pulses of NIR exposure may be used at desired time intervals so that the cargo is released in steps.

The composition comprising the nanovesicles in a suitable carrier can be administered to individuals by any suitable route. In one embodiment, it is administered by intravenous infusion such that it will enter the vasculature (circulatory system). The composition may be administered systemically or may be administered directly into the blood supply for a particular organ or tissue or tumor. When irradiated by NIR, the contents of the PoP-NVs may be released within the circulatory system and may then enter the surrounding tissue. In certain embodiments, the PoP-NVs may be directly provided to the relevant tissue.

An advantage of PoP-NVs is that they function through nanoscale heating, rather than bulk heating. Nanoscale heating allows effective release from the PoP-NVs without any significant heating of the surrounding tissue. Thus, in an example, rapid release of the entire cargo in three minutes upon (0.1 W) NIR laser irradiation was achieved. These same PoP-NVs showed minimal release over 30 minutes at 45° C. (a temperature higher what is required for Temperature sensitive liposomes (TS-liposomes) to rapidly release their entire contents) and do not even completely release their entire cargo when heated to the extreme temperature of 95° C. for 30 minutes. Thus, PoP-NVs are unique because they demonstrate extremely effective light-induced release, yet are exceptionally stable at elevated temperatures. At least these two attributes combine to form the basis of a precisely triggered drug release mechanism.

Additionally, the serum stability of the PoP-NVs enables longer time point options for triggered release (less stable delivery systems must be triggered immediately following administration).

In one embodiment, the present disclosure provides a nanovesicle comprising a bilayer of at least 1 mol. %, from 1 to 14 mol. %, 7 to 13 mol. %, 8 to 12 mol. %, 9 to 11 mol. %, or 9.5 to 10.5 mol. % porphyrin phospholipid conjugate, wherein the porphyrin phospholipid conjugate has the structure of Compound A. In another embodiment, the present disclosure provides a nanovesicle comprising a bilayer of at least 1 mol. %, 1 to 14 mol. %, 7 to 13 mol. %, 8 to 12 mol. %, 9 to 11 mol. %, or 9.5 to 10.5 mol.% porphyrin phospholipid conjugate, wherein the porphyrin phospholipid conjugate has the structure of PC-HPPH-C16 (Compound B), Compound C, or Compound D. In one embodiment, the present disclosure provides compositions comprising the nanovesicles in a suitable carrier. In another embodiment, the present disclosure provides a method of delivering an agent to a desired site comprising the steps of: loading the agent as a cargo in the PoP-NVs of the present disclosure, administering the PoP-NVs to an individual, causing the release of the cargo (agent) at desired sites by shining near infra-red radiation as the nanovesicles are passing through the vasculature at the desired site such that the cargo from the nanovesicles is released. In one embodiment, upon shining the NIR radiation, the cargo (agent) release is achieved when the nanovesicles are moving through small blood vessels (such as capillaries). In one embodiment, upon shining the NIR radiation, the cargo is released when the blood flow is from 0.5 to 10 mm/sec. In this manner, drug release may be confined only to smaller vessels in the target tissues and not nearby larger blood vessels.

The following examples are presented to illustrate the present disclosure. They are not intended to limiting in any manner.

EXAMPLE 1

This example describes the synthesis of PoP-NVs, and loading and release of cargo.
Methods
Synthesis of PoP-NVs: In this example, Pyropheophorbide-a hexyl ether (HPPH)-lipid was used as a stable PoP-NV doping agent. HPPH phospholipid was synthesized using commercially available HPPH and esterifying it 1-palmitoyl-2-hydroxy-sn-glycero-3-phosphocholine (lyso-C16-PC, Avanti # 855675P) using EDC and 4-Dimethylaminopyridine (DMAP; Fisher # AC14827-0250) in chloroform at a 1:1:2:2 Tyco-C16-PC:HPPH:EDC:DMAP molar ratio. The resulting HPPH phospholipid was purified with diol silica gel and freeze dried in a 80% t-butanol (Sigma, #360538), 20% water solution. Purity was confirmed with TLC (>90% pure) and identity confirmed with mass spectrometry. To generate PoP-NVs, a 0.5-2 mg solution comprising the lipids was created in chloroform, evaporated, re-hydrated with phosphate buffered saline, subjected to 5 freeze-thaw cycles and sonicated for 10 minutes. In the case of extrusion, the solution was subjected to 11 passes through a 100 nm polycarbonate membrane.

Cargo loading and release of PoP-NVs: Calcein loading was achieved by hydrating PoP-NVs with a 100 mM calcein solution (Sigma# 21030) and subsequent gel-filtration separation over a Sephadex G-75 column (VWR# 95016-784). Doxorubicin loading was achieved by extruding a lipid film with a high pressure lipid extruder (Lipex) with a 150 mM ammonium sulfate solution. Free ammonium sulfate was removed using a Sephadex G-75 column and doxorubicin (LCLabs# D-4000) was loaded by adding a 1:10 ratio of drug:lipid and incubating at 60° C. for 1 hour. Free doxorubicin was removed using a Sephadex G-75 column For release experiments, PoP-NV solutions of 0.5-2 mg/mL were generally diluted by a factor of 50-100 for calcein experiments, and 10-20 times for doxorubicin release, to a point where light could pass freely through the solution. Release experiments were performed using a hand-held laser diode outputting 120 mW or a tunable 658 nm 500 mW laser diode (LaserGlow). Irradiations were performed as indicated. Temperature was measured by inserting a K-type thermocouple probe directly into the irradiated solution. Calcein release was assessed by measuring the release before and after treatment, including solubilisation with 0.1% Triton X-100. Release was calculated using the formula Release=(Ffinal-Finit)/(FTX100-Finit)*100%. Cargo release using varying flow speeds was performed using a syringe pump.

Figure 1:
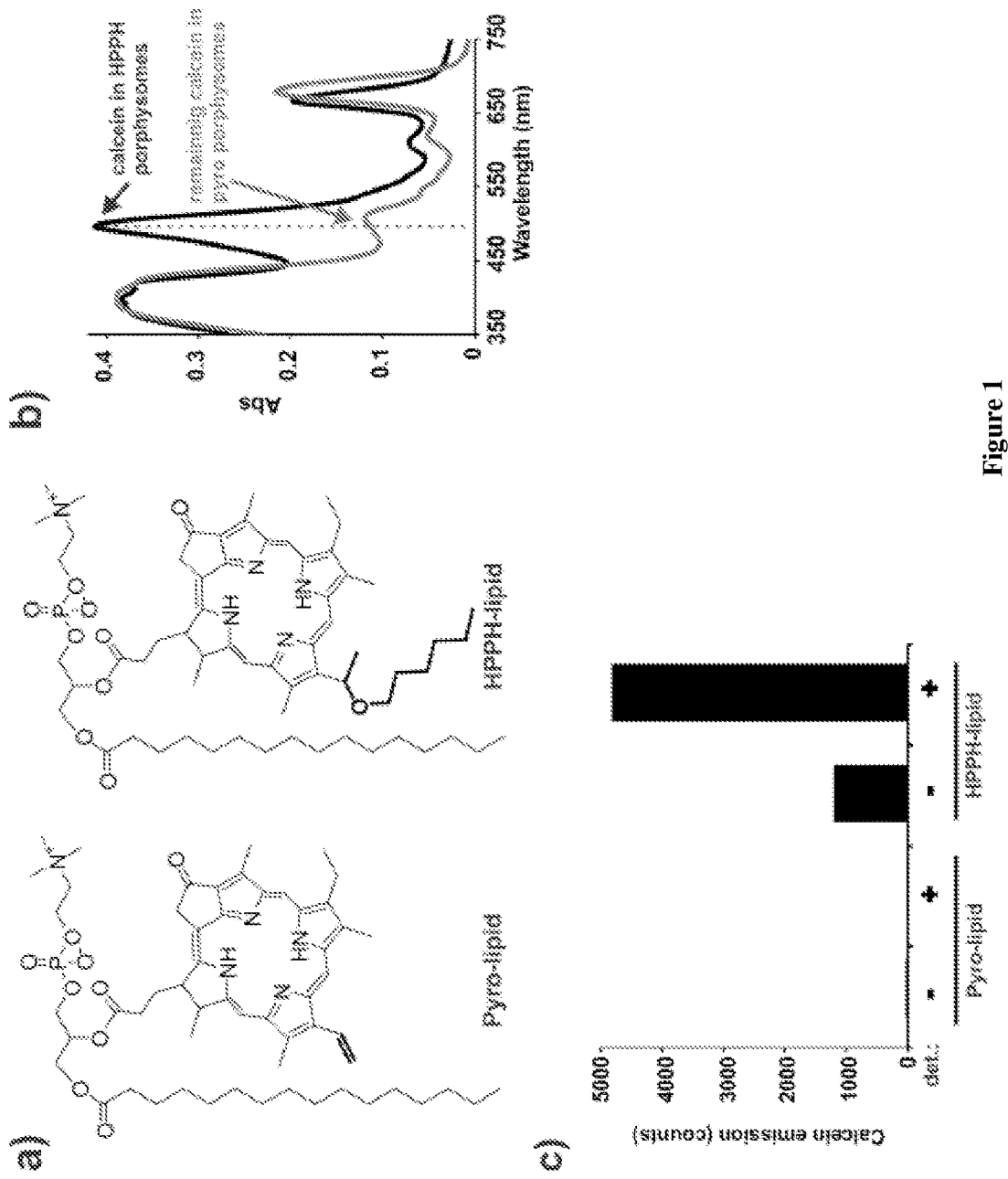
FIG. 1. 5. C LQ-BIC solar cells with R A monomer for porphyrin bilayer capable of stable cargo loading. a) Chemical structures of pyro-lipid and HPPH (Pyropheophorbide-a hexyl ether) phospholipid. b) Absorption spectra of isolated nanovesicles formed from either monomer and loaded with calcein. c) Stable cargo retention from bilayers of HPPH phospholipid (also referred to as HPPH-lipid in this disclosure), but not pyro-lipid. Both monomers were synthesized, and assembled into nanovesicles loaded with calcein at self-quenching concentrations. Nanovesicles were separated from unentrapped calcein prior to assessing fluorescence. Fluorescence emission of retained calcein in nanovesicles is shown prior or following addition of 0.25% Triton X-100 (Det.).

Results
The structure of pyropheophorbide-C16-phosphtatidylcholine monomer and HPPH-C16-PC are shown in FIG. 1a. HPPH is related to the pyro structure, but appears to generate greater balance between sidechains and also is a clinically approved porphyrin therapeutic. HPPH-C16-PC was synthesized and the behavior of nanovesicles formed from 95% of either porphyrin monomer along with 5% PEG-lipid was examined. As shown in FIG. 1b, when loaded with calcein, a clear calcein peak was apparent in the absorption spectra of the isolated HPPH phospholipid NVs (also referred to as porphysomes), but not those formed from Pyro-phospholipid (referred to as pyro-porphysomes). FIG. 1c demonstrates that calcein maintains self-quenching concentration in the HPPH NVs, but no retained calcein was detectable in the pyro-NVs.

Figure 2:
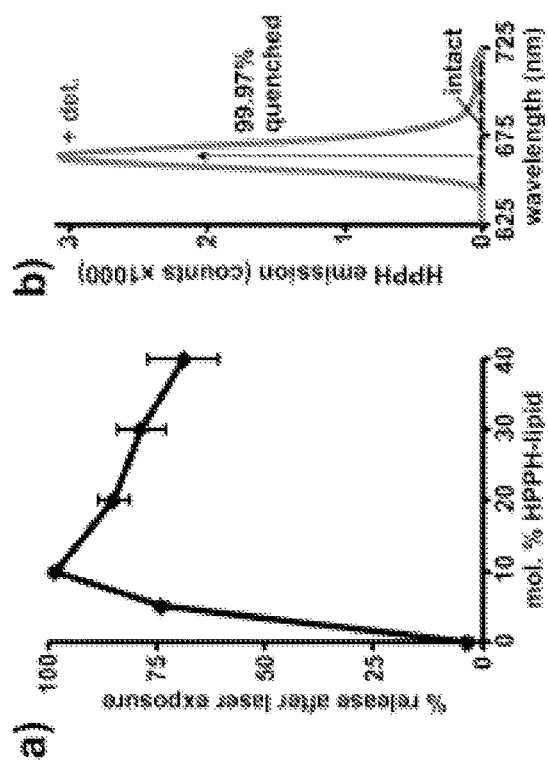
FIG. 2. Example of porphyrin-phospholipid doping for optimized NIR light-mediated permeabilization. a) PoP-NVs were formed from 5% PEG2K (PEG=polyethylene gloycol) lipid, 35% cholesterol, and 60% DSPC. HPPH phospholipid was titrated in place of 1,2-Distearoyl-sn-glycero-3-phosphocholine (DSPC) as indicated. b) Porphyrin-phospholipid exhibit 99.97% self-quenching (comparing intact vs detergent disrupted).
Figure 3:
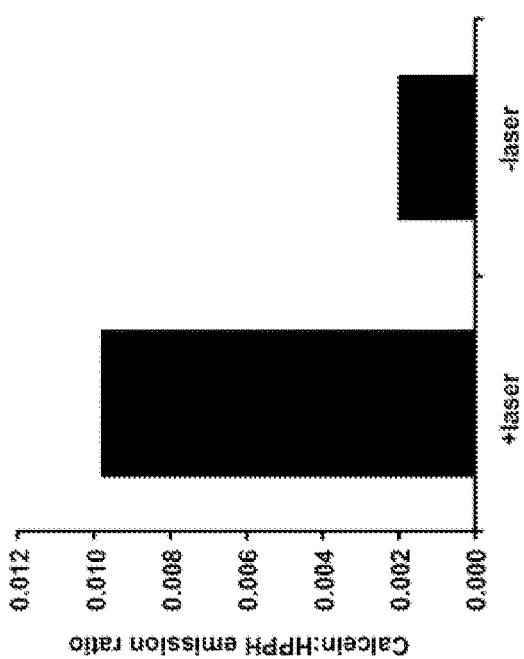
FIG. 3. Example of laser-loading of PoP-NVs. PoP-NVs were incubated in a 2 mM calcein solution and irradiated with 120 mW, 658 nm laser irradiation for 3 minutes. Free calcein and PoP-NV entrapped calcein were separated with gel filtration and the ratio of calcein emission to HPPH phospholipid emission (using separate excitation and emission settings) was measured.
Figure 4:
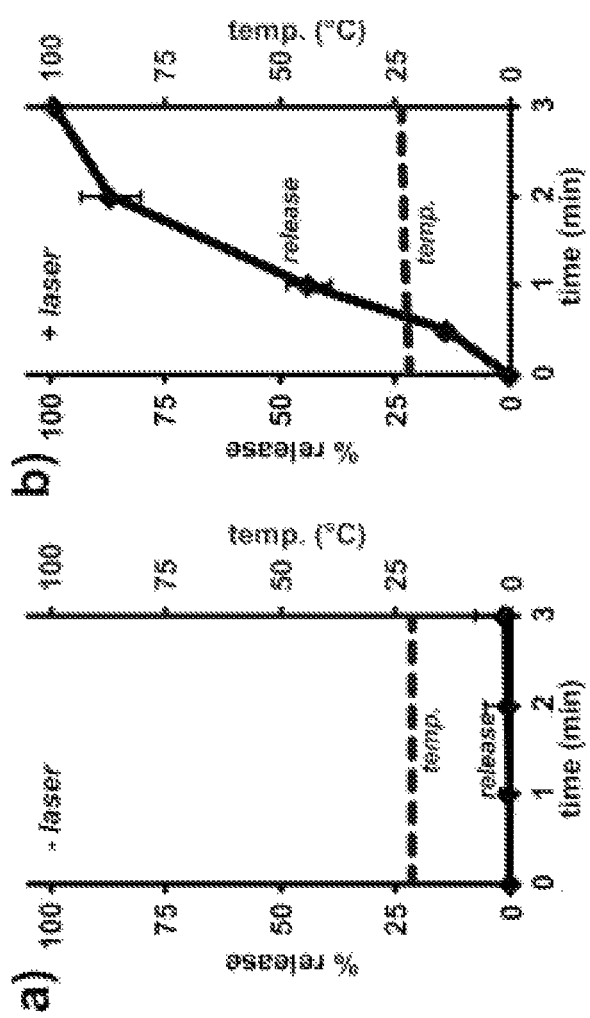
FIG. 4. Demonstration of permeabilization occurs without bulk solution heating.

Next, we examined how mild NIR irradiation (3 min, 120 mW using a 658 nm laser) would affect entrapment efficacy of liposomes, as increasing amounts of HPPH phospholipid monomer were incorporated. A starting point of 5% PEG-lipid, 35% cholesterol and 60% DSPC was utilized, which is similar to the stable commercial lipodox formulation, and incrementally replaced DSPC for HPPH phospholipid. Without HPPH phospholipid doping, the NVs remained fully loaded following NIR irradiation. However, when only 10 molar percent HPPH phospholipid was included in the PoP-NVs, complete cargo release was observed following irradiation (FIG. 2a). Unexpectedly, as a greater portion of HPPH phospholipid was titrated into the PoP-NVs, the amount of light-induced permeabilization steadily decreased, despite the higher optical character of the bilayer and greater light absorption of the NVs. At 10% HPPH phospholipid, PoP-NVs were essentially completely self-quenched (FIG. 2b). Porphyrin fluorescence self-quenching correlates directly to singlet oxygen self-quenching, and therefore within the quenched porphyrin bilayer of PoP-NVs, no photosensitized chemical reactions took place to induce the release. FIG. 3 demonstrates that NIR laser exposure can be used to induce PoP-NV permeability in such a calcein-containing solution to allow loading (as opposed to release), of cargo, which further points to the stability and inertness of PoP-NVs during the permeabilization process. The kinetics of NIR laser induced release while monitoring the solution temperature was examined. In the absence of laser irradiation, solution temperature remained constant and there was no release from PoP-NVs (FIG. 4a). When exposed to laser irradiation, PoP-NVs released their cargo over the course of 3 minutes (FIG. 4b). Remarkably, release from PoP-NVs occurred with minimal change in bulk solution heating, ruling out a conventional DSPC or DPPC phase transition mechanism. Indeed, as shown in FIG. 5, in the absence of irradiation, PoP-NVs could stably retain their loaded cargo at 40, 60 and even 90° C.

The 10 molar % HPPH phospholipid conferred thermal stability because without it, liposomes exhibited significantly higher release at 60 and 90° C. Because optimal doping in PoP-NVs used only 10 molar % porphyrin, it was possible to directly compare NVs composed nearly identically, with the only difference being the inclusion of 10 molar percent of either free HPPH or HPPH phospholipid. Both types of nanovesicles could be formed and stably entrapped calcein. Both types of nanovesicles also exhibited nearly complete quenching of HPPH fluorescence. Although liposomes formed with free HPPH displayed some light specific release, as shown in FIG. 6a, PoP-NVs were over 5 times more effective at releasing cargo in response to light and were approximately 150 times more effective when the ratio of release with and without light irradiation is considered. FIG. 6b demonstrates that when incubated with 10% fetal bovine serum, free HPPH readily transfers from liposomes to serum proteins whereas PoP-NVs remain self-quenched indicated a lack of exchange.

Next, we examined whether PoP-NVs could be actively loaded with doxorubicin. As shown in FIG. 7a, doxorubicin could be loaded using an ammonium sulfate gradient with over 95% efficacy. As shown in FIG. 7b, when dox-PoP-NVs were irradiated with varying powers of laser in a buffer including 10% serum, release occurred in a laser dose dependent manner. This controllable release has direct utility for controlling the release in vivo to achieve maximal release in the tumor microenvironment. As shown in FIG. 8, the velocity of flow through capillaries had a direct effect on the light-induced release from PoP-NVs. The data in FIG. 9 shows laser exposure can trigger a significant increase the rate of release of entrapped doxorubicin (in this case a 20,000 fold increase) in physiological conditions (in this case 10% serum, 37 C).

PoP-NVs represent a robust nanosystem to achieve light-induced release. Permeabilization occurred in the absence of checmial reactions or bulk solution heating. By varying the laser power, the amount of release could readily be tuned. Unlike release systems that rely directly or indirectly on heating through phase transitions, PoP-NVs offer a high level of control over permeabilization. It is considered that PoP-NVs will be useful in stimuli driven release for treatment of various indications including cancer.

EXAMPLE 2

This example further describe the experiments with PoP-NVs. An externally-controlled drug release system based on liposomes doped with porphyrin-phospholipid (PoP) and triggered directly by near infrared (NIR) light was used. Molecular dynamics simulations of porphyrin bilayers identified a novel light-absorbing PoP monomer esterified from clinically approved components predicted and experimentally demonstrated to give rise to a more stable bilayer. Membrane permeabilization could be induced upon exposure to NIR irradiation with liposomal inclusion of 10 molar % PoP and occurred in the absence of bulk or nanoscale heating. Liposomes re-sealed following laser exposure and permeability could be modulated by varying porphyrin-lipid doping, irradiation intensity or irradiation duration. PoP-liposomes demonstrated spatial control of release of entrapped gentamicin and temporal control of release of entrapped fluorophores following intratumoral injection. Following systemic administration, laser irradiation enhanced deposition of actively-loaded doxorubicin in mouse xenografts, enabling an effective single-treatment anti-tumor therapy.

Methods: Molecular dynamic simulations: Membranes made of two different porphyrin-lipid molecules were simulated using molecular dynamics (MD). Each bilayer system was composed of 128 molecules of either the pyro or HPPH variant of the porphyrin-lipids. 9640 water molecules were added to achieve full hydration. The GROMACS software package was used. Starting with the standard united atom force field, the lipid models were defined by removing the sn-2 tail from DPPC and replacing it with the heme available in the force field database. GROMOS 53a6 force-field was used to build the final structures and to modify the heme. This force-field has been shown to perform well in simulations of lipids and peptides. Partial charges were chosen from analagous moieties in the force field database. The simple point charge (SPC) model was used for water. Bond lengths were constrained using the SETTLE algorithm for water and LINCS for the lipids. Lennard-Jones interactions were treated with a switching algorithm that started at 0.8 nm and used a cutoff of 0.9 nm. Electrostatics were treated with the particle-mesh Ewald method using a real space cutoff of 1.4 nm, beta spline interpolation (of order 4), and a direct sum tolerance of 1E-6. Periodic boundaries were used in all three dimensions and a time step of 2 fs was used. The systems were set up by arranging 64 lipids per leaflet on a rectangular lattice. Steepest decent energy minimization was done before adding water and then repeated. This was followed by 100 ps of NVT relaxation at 273.15 K using a stochastic dynamics integrator and 100 ps of NpT relaxation at 310.15 K. As the final part of relaxation, a 500 ns NpT simulation was run at 310.15 K and 1 bar. Leaf-frog integrator was used. The production simulations were conducted in the NpT ensemble. Pressure and temperature were fixed at 1 bar and 310.15 K, respectively, using the Parrinello-Rahman algorithm with a relaxation time of 0.5 ps for pressure and the velocity resealing algorithm for temperature coupling with a relaxation time of 0.1 ps. The temperatures of the lipids and water were coupled independently. This simulation protocol has been shown to be reliable for membrane systems.

Synthesis of PoP-liposomes: Pyro-lipid was synthesized as previously described (Lovell et al., Proc. Natl. Acad. Sci., USA, 102:17975-17980, 2005). HPPH phospholipid was synthesized using by esterifying HPPH (purified as previously described) at room temperature with 1-palmitoyl-2-hydroxy-sn-glycero-3-phosphocholine (lyso-C16-PC, Avanti #855675P) using EDC and 4- Dimethylaminopyridine (DMAP; Fisher #AC14827-0250) in chloroform at a 1:1:2:2 lyso-C16-PC:HPPH:EDC:DMAP molar ratio. The resulting HPPH phospholipid was purified with diol silica gel and freeze dried in a 80% t-butanol (Sigma #360538), 20% water solution. Purity was confirmed with TLC (>95% pure) and identity confirmed with mass spectrometry (expected 1114.7; found: 1114.7) and 1H NMR on a Varian Inova 500 MHz spectrometer. To generate PoP-liposomes, films were prepared by drying chloroform solutions containing 1,2-distearoyl-sn-glycero-3-phosphocholine (DSPC; Avanti #850365P), 1,2-distearoyl-sn-glycero-3-phosphoethanolamine-N-[methoxy(polyethylene glycol)-2000 (DSPE-PEG2K; Avanti #880120P), HPPH phospholipid and cholesterol (Avanti #700000P) in the indicated molar ratios. The general formulation for PoP-liposomes was based on 50 mol. % DSPC, 35 mol. % cholesterol, 10 mol. % HPPH phospholipid and 5 mol. % DSPE-PEG2K. Liposomes incorporating 10 mol. % free HPPH were formed analogously. The chloroform was evaporated using either a stream of argon gas or a rotary evaporator followed by further drying in a dessicator vacuum chamber. The film was re-hydrated with phosphate buffered saline (pH 7.4) and sonicated for 30 minutes.

Cargo release and loading from PoP-liposomes: Self-quenching dye loading was achieved by hydrating and sonicating PoP-liposomes with a 100 mM calcein solution (Sigma #21030) or sulforhodamine B solution (VWR #89139-502) and subsequent gel-filtration separation over a Sephadex G-75 column (VWR #95016-784). Doxorubicin loading was achieved by extruding a lipid film with a high pressure lipid extruder (Northern Lipids) with a 250 mM ammonium sulfate solution. Polycarbonate membranes of 0.2, 0.1 and 0.08 μm pore size were sequentially stacked and solution was passed through the extruder 10 times at 60° C. Free ammonium sulfate was removed by overnight dialysis in a 10% sucrose solution with 10 mM HEPES pH 7.4. Doxorubicin (LC Labs #D-4000) was then loaded by adding a 1:10 ratio of drug:lipid and incubating at 60° C. for 1 hour. Free doxorubicin was removed by dialysis. For release experiments, PoP-liposome solutions of 0.5-2 mg/mL were generally diluted by a factor of 50-100 for calcein experiments, and 10-20 times for doxorubicin release, and light could pass freely through the solution without inner filter effects. Release experiments were performed using a hand-held laser diode outputting 120 mW at 658 nm or a tunable 658 nm 500 mW laser diode (LaserGlow) and irradiations were performed as indicated. When incubated in serum, fetal bovine serum was used (VWR #16777-532). Temperature was measured by inserting a K-type thermocouple probe directly into the solution during irradiation. Cargo release was assessed by measuring the release before and after treatment, including solubilisation with 0.25% Triton X-100. Release was calculated using the formula Release=$(F_{FINAL}-F_{INIT})/(F_{TX100}-F_{INIT})*100\%$. OriginPro 8.5 was used for data fitting where equations are indicated. A Zetasizer ZS90 (Malvern Instruments) was used for dynamic light scattering analysis. For spatial control of release experiments, a 1 agarose gel was doped with sulforhodamine B loaded PoP-liposomes when the agarose had been melted and cooled to ~50° C., prior to solidification. Release was then performed using 658 nm laser irradiation with a preformed mask printed on transparency paper. The agarose was imaged using an IVIS Lumina II system. Cargo release using varying flow speeds was performed in tygon tubing with a 0.3 mm inner diameter and a variable speed syringe pump operating at the indicated speeds (New Era, #NE-1000). For Amphotericin B loading, Amphotericin B (VWR # 97061-610) liposomes were formed using the thin film method using a lipid formulations of the indicated molar ratios composed of 1,2-distearoyl-sn-glycero-3-phospho-(1'-rac-glycerol) (DSPG; Avanti #840465X), hydrogenated soy phosphatidylcholine (Avanti #840058P), HPPH phospholipid and cholesterol. Following liposome formulation via sonication, solutions were filtered and the amount of Amphotericin B in the filtrate and pre-filtered solution were determined using fluorescence with 365 nm excitation and 470 nm emission.

Cell viability experiments: In vitro cell studies were performed by seeding 10,000 Panc-1 cells per well in a 96 well plate. Drug (10 μg/mL doxorubicin in free or PoP-liposomal form and/or an equivalent amount of empty PoP-liposomes based on HPPH phospholipid concentration) was added as indicated in media (DMEM, VWR #16777-200) containing 10% fetal bovine serum. The wells were irradiated as indicated using a 658 nm laser with 200 mW/cm² fluence rate for 5 minutes. Drugs and media were left to incubate in media containing serum without removal for 24 hours. After 24 hours, media was replaced and cell viability was assessed 24 hours later using the XTT assay (VWR #89138-264). Viability was calculated by measuring absorption at 450 nm subtracting a 630 nm background reading and normalizing to untreated control cells using a Safire plate reader (TECAN).

Cryo-electron microscopy: To perform the cryo-EM experiments 3.4 μL of sample were deposited in a c-flat™ grids (CF-2/2-2C) with an additional continuous layer of thin carbon (5-10 nm). Grids were glow discharged in air at 5 mA for 15 seconds prior to sample addition. Samples contained the dox-PoP liposomes before and after irradiation at a concentration of 5 mg/mL (dox concentration ~1.5 mg/mL) in a buffer with 10 mM HEPES (pH 7.4) and 10% sucrose. Grids were blotted twice and vitrified by rapidly plunging them into liquid ethane at −180° C. using a Vitrobot (FEI). The blotting chamber of the Vitrobot was set up at 25° C. and 100% relative humidity. Grids were transferred to a JEOL 2010F electron microscope operated at 200 kV using a Gatan 914 cryo-holder. Images were recorded on Kodak SO-163 films under low dose conditions (~15-20 e/Å2) at a nominal magnification of 50,000× and a defocus of −5 μm. Electron micrographs were digitized with a step size of 12.7 μm in a Nikon Super Coolscan 9000 scanner producing images with a sampling value of 2.54 Å/pixel.

Electron spin resonance: PoP-liposomes were formed with the inclusion 1% 5-Doxyl steric acid (Sigma #253634) into the standard formulation using the thin film hydration method. A Bruker ER-200 ESR X-band spectrometer was used with a TE102 rectangular cavity and with a Bruker B-VT-1000 nitrogen flow temperature controller. The ESR frequency was 9.44 GHz, field modulation of 1.9 Gauss, and microwave power of 0.64 mWatt. The sample size was approximately 20 μL in a 1 mm inner diameter quartz tube at the indicated temperatures. Samples were irradiated using a 658 nm 200 mW laser that was focused on the ESR sample through light slots on the Bruker X-band ESR cavity, which are conditions that induce PoP-liposome permeabilization.

Confocal Microscopy: 10,000 Panc-1 cells were seeded in 8 well confocal chamber slides (VWR #43300-774) in DMEM media with 10% serum. 24 hours later, cells were incubated with 10 μg/mL doxorubicin in either free or PoP-liposomal form in DMEM in 10% serum. Laser treatment was performed as indicated and all wells were incubated for an additional 3 hours. Media was replaced and cell imaging was performed using a Zeiss LSM 710 confocal microscope with 20× objective using 490 nm excitation and 612 nm emission.

Bacteria killing experiments: PoP-liposomes formed using the thin film method were passively loaded in a solution of 85 mg/mL gentamicin sulfate (Fisher #BP918-1). Following sonication, non-entrapped gentamicin was removed with gel filtration over a Sephadex G-75 column Gentamicin concentration in the liposomes was determined using a fluorescent assay as previously reported. *B. Subtilis* (Cm+) was grown overnight in liquid LB medium at 37° C. overnight. PoP-liposomes and the liquid bacteria culture were combined with melted LB agar in a volume ratio of 1:30. The temperature of the agar was ~45° C. when with *B. Subtilis* and the PoP-liposomes. The plates were poured with about 5 mL of bacteria-drug-agar per plate. Following solidification, the plates were irradiated with a 1.2 cm spot diameter with 200 mW/cm² for 10 minutes using a 658 nm laser. The plate was photographed 24 hours later.

Liposomal release from tumors following intratumoral administration: Panc-1 tumors were grown by injecting 20 g female nude mice (Charles River) with 3×10⁶ Panc-1 cells in a 1:1 matrigel dilution (BD Biosciences) in the hind flank of the mice. Following several weeks of growth, the tumors were carefully injected intratumorally with sulforhodamine B-PoP-liposomes. Images were acquired with an in vivo fluorescence imager (IVIS Lumina II) at the indicated time points with the mice under isoflurane-induced anesthesia. The tumor was irradiated for 30 minutes with a 0.6 cm diameter spot size at 200 mW/cm$^2$ power density and mice were imaged again.

Systemically-administered treatments: KB cells (Hela subline) were injected in the right flank of female nude mice (Jackson Labs). When tumor volumes reached 4-6 mm in diameter, dox-PoP-liposomes (10 mg/kg dox) or an equivalent dose of empty PoP-liposomes were injected via tail-vein. 10-15 minutes later, tumors were irradiated for 12.5 minutes with a 200 mW/cm$^2$ laser (150 J/cm$^2$). For biodistribution studies, mice were sacrificed 24 hours later, tissues homogenized, extracted overnight in acidic isopropanol and dox (Doxorubicin) biodistribution was determined via fluorescence measurements with 480 nm excitation and 590 nm emission. For survival studies, tumor size was monitored 2-3 times per week and mice were sacrificed when the tumor grew to 1 cm in any dimension.

For pharmacokinetic analysis, male BALB/c mice were injected via tail vein with empty PoP-liposomes (15 mg/kg HPPH phospholipid). Small blood volumes were sampled at sub-mandibular and retro-orbital locations at the indicated time points and serum was analyzed for HPPH content using fluorescence with 400 nm excitation and 660 nm emission following dilution into a 0.25% Triton-X100 solution to prevent any self-quenching.

We observed that PoP can self-assemble into liposome-like porphysome nanovesicles formed entirely from a porphyrin bilayer with intrinsic biophotonic character, nanoscale optical properties, biocompatibility and biodegradability. However, previously described porphysome monomers cannot assemble into nanovesicles that stably load and retain cargo without addition of cholesterol. To overcome this shortcoming, the structure of the sn-1-palmitoyl sn-2-pyropheophorbide phosphtatidylcholine (pyro-lipid) monomer was examined. We investigated if devinyl hexyloxyethy-pyropheophorbide (HPPH) based monomers might form bilayers with superior self-assembly and packing properties.

To investigate if HPPH phospholipid based nanovesicles might enable better cargo loading, we used molecular dynamics (MD) simulations. MD simulations have been shown to be useful for determining molecular and supra-molecular physical properties of lipid bilayers. The existing porphyrin was modified and lipid force fields to generate the porphyrin-lipid parameters and performed MD simulations with a bilayer system composed of 128 molecules of either pyro-lipid or HPPH phospholipid (labeled in some figures as "HPPH-lipid"). Water was added to produce a 3 nm layer between periodic images of the membrane, which required an average of 9640 water molecules per system. As shown in FIG. 10a, the bilayer density plot revealed that the HPPH phospholipid did not give rise to a bilayer with greater maximum density, but rather a thicker bilayer (3.2 vs 2.9 nm with the Gibbs-Luzzati criterion). MD simulations showed the hexyl ether moiety provides space filling between the two bilayer leaflets compared to the pyro-lipid bilayer which had the central portion of the bilayer filled only with palmitoyl chains. An extended (>500 ns) duration MD simulation of the HPPH phospholipid bilayer with the hexylether moitey. The porphyrins in the pyro-lipid bilayer appeared to align into stacks of H-aggregates, which may contribute to instability. Intermolecular porphyrin-lipid interactions were assessed using intermolecular hydrogen bonding. Both Pyro and HPPH phospholipids contain two hydrogen bond donors located in the porphyrin ring and hydrogen bond acceptors located both in the porphyrin ring and the oxygens in the esters of the glycerol backbone and the oxygens on the phosphate. As shown in FIG. 10b, both pyro-lipid and HPPH phospholipid formed bilayers with an approximate equivalent amount of total hydrogen bonds. However, there was a significantly greater fraction of intermolecular hydrogen bonds in the pyro-lipid bilayer (59% vs 43%). This reflects the propensity for the pyro-lipid bilayer to form face-to-face stacks within the bilayer that may contribute to instability in retaining loaded cargo. The chain order parameter (Szz) indicates the orientation of the lipid chain with respect to the bilayer normal. Values near 1 indicate an average orientation parallel to the bilayer normal and values closer to zero indicate an orientation angled close to 45 degrees away from bilayer normal. The terminal positions of the sn-1 palmitoyl chains in HPPH phospholipid bilayers were more ordered, as shown in FIG. 10c. Thus, MD simulations suggested that HPPH phospholipid bilayers might have enhanced stability compared to pyro-lipid bilayers due to a slightly thicker bilayer, less intermolecular aggregate formation and more ordering in the palmitoyl side-chains.

Successful synthesis of HPPH phospholipid was achieved. Next, the behavior of nanovesicles formed from either pyro-lipid or HPPH phospholipid, along with 5 molar % PEG-lipid to enhance physiological properties was experimentally examined. As previously observed, pyro-lipid nanovesicles hydrated with a 100 mM calcein solution could not stably retain the fluorophore, which was not detectable following nanovesicle isolation (FIG. 10b). However, nanovesicles formed from HPPH phospholipid entrapped calcein with high retention efficacy so that it remained self-quenched in the nanovesicles prior to permeabilization with 0.25% Triton X-100 detergent. Thus, MD simulations correctly predicted a more stable bilayer from HPPH phospholipid, which was demonstrated experimentally to enable robust entrapment of cargo inside the nanovesicles.

With stable cargo loading made possible by the development of HPPH phospholipid, we determined whether NIR irradiation at the specific absorption peak of HPPH could cause the release of loaded cargo. Calcein was entrapped at self-quenching concentrations and a 658 nm laser was used to irradiate samples for 3 minutes at 120 mW (240 mW/cm$^2$ power density). A starting point of 5% distearoylphosphatidylethanolamine-polyethylene glycol 2000 (PEG-lipid), 35% cholesterol and 60% distearoylphosphatidylcholine (DSPC) was selected since this formulation is similar to stable and clinically proven liposomal doxorubicin formulations, and then DSPC was incrementally replaced with HPPH phospholipid. Without any HPPH phospholipid doping, the liposomes remained fully loaded following laser irradiation. However, when only 10 molar % HPPH phospholipid was included, complete cargo release was observed following irradiation (FIG. 2a). Unexpectedly, as a greater portion of HPPH phospholipid was titrated into the PoP-liposomes, the amount of light-induced permeabilization decreased, despite the higher optical character of the bilayer. Thus, beyond an optimal portion, HPPH phospholipid had a stabilizing effect on cargo retention in PoP-liposomes in response to laser irradiation. The kinetics of NIR laser induced release were examined while simultaneously monitoring the solution temperature. In the absence of laser irradiation, the solution temperature remained constant at room temperature and there was no cargo release (FIG. 4a). As PoP-liposomes were exposed to NIR irradiation, cargo was released steadily and completely over the course of 3 minutes (FIG. 4b). Release from PoP-liposomes occurred without any significant increase in the solution temperature. This was unexpected and represents a departure from conventional triggered liposomal release mechanisms which rely on solution heating to trigger phase transitions. Although no heating was observed based on inserted thermocouple measurements, heating occurring directly at the PoP-liposome bilayer could not be ruled out based on bulk solution measurements alone. To assess local heating, 1 molar % of 5-doxyl steric acid spin label (5-DSA), a commonly used electron spin resonance (ESR) probe that measures temperature-related bilayer fluidity, was incorporated based on probe tumbling rate. 5-DSA that was incorporated into PoP-liposomes produced a characteristic ESR spectrum with one central peak flanked by smaller ones (FIG. 11a). As shown in FIG. 11b, the peak width of the central feature narrowed at elevated temperatures, as is expected for a nitroxide spin label due to increased tumbling rates. Thus, 5-DSA provided a means to assess nanoscale heating during laser irradiation. By measuring the peak-to-trough width of the central spectral feature, nanoscale thermal analysis of bilayer heating during laser irradiation was possible (FIG. 11c). Based on thermally calibrated ESR measurements, during laser irradiation conditions that permeabilized the PoP-liposomes, there was no appreciable bilayer heating (a change of less than 0.5° C.).

Since NIR-induced permeabilization was not driven by laser-induced bulk or nanoscale heating effects, the thermal stability of PoP-liposomes in externally heated solutions was examined. Previously, it has been shown that porphyrin-lipid and cholesterol-lipid conjugates attenuate temperature-induced lipid bilayer phase transitions (that destabilize membranes). As shown in FIG. 5, in the absence of irradiation, PoP-liposomes could stably retain their loaded cargo at 40, 60 and even 90° C. This provides further evidence that a temperature-related phase transition based mechanism is not responsible for the light-induced release. The thermostability enabled PoP-liposomes loaded with sulforhodamine B to be incorporated into hot agarose (~50 ° C.) prior to solidification without leakage. A 658 nm laser could be used to achieve excellent spatial control of permeabilization and release of sulforhodamine B within the solidified agarose (FIG. 12). To gain insight on the nature of the light-induced release, it was examined whether HPPH phospholipid was specifically contributing to release via concerted supramolecular effects, or whether HPPH phospholipid was acting simply as a light-absorbing photothermal transducing component within the bilayer. Liposome formation becomes physically impossible and large aggregation occurred when more than 15 molar % free porphyrin is included into the formulation. However, because optimal doping in PoP-liposomes used only 10 molar % porphyrin, it was possible to directly compare liposomes composed identically except for the inclusion of 10 molar % of either free HPPH or HPPH phospholipid. Gel filtration demonstrated that free HPPH, which has minimal water solubility, fully incorporated into the liposomes (FIG. 17). Both types of liposomes could be formed and stably entrapped calcein. Both types of liposomes exhibited HPPH fluorescence quenching of over 90% compared to the detergent-disrupted liposomes (FIG. 18), creating a comparative system since fluorescence self-quenching is correlated to downstream events such as quenching of singlet oxygen generation. When irradiated with NIR light, liposomes containing free HPPH displayed limited light-induced release and PoP-liposomes were over 5 times more effective at releasing cargo (FIG. 6a). Considering the high background leakage rate of liposomes containing free HPPH, PoP-liposomes were 150 times more effective with respect to the ratio of release following laser irradiation to release in the absence of triggering stimuli. This demonstrates that the constraints conferred by the HPPH phospholipid within the porphyrin bilayer play an active role in the release. The presence of 10 molar % HPPH phospholipid in the bilayer did not inhibit the solubilization of a membrane-partitioning drug, amphotericin B into a clinically-used formulation of that drug (FIG. 19). Any NIR chromophore (including free HPPH) could be loaded into liposome bilayers and be used to induce some degree of light-responsive release. When incubated with serum, free HPPH incorporated into liposomes rapidly transferred to serum components and became completely fluorescently unquenched within 30 minutes (FIG. 6b). In contrast, PoP-liposomes remained self-quenched, indicating a lack of detectable exchange of HPPH phospholipid with serum components. Following intravenous administration in BALB/c mice, PoP-liposomes exhibited a long single compartment circulation half-life of 14.4 hours (FIG. 20). This is similar to previously observed 12-13 hour one compartment circulation half-life of porphysome nanovesicles containing 60 molar % pyro-lipid, yet somewhat shorter than some formulations of sterically-stabilized PEGylated liposomes for doxorubicin delivery, which can exhibit 20 hour circulation half-lives in mice.

To emphasize spatial and temporal control of release and demonstrate wide-ranging utility of PoP-liposomes, experiments for antibacterial and antineoplastic applications were developed. Liposomes have attractive properties for antibacterial drug delivery and gentamicin, a common aminoglycoside antibiotic, could be passively loaded into the interior of PoP-liposomes. Due to their thermal stability, gentamicin-PoP-liposomes could be impregnated into hot agar prior to solidification along with *Bacillus subtilis*, a model gram positive bacteria. As shown in FIG. 13a, when impregnated with 10 μg/mL gentamicin-PoP-liposomes (based on gentamicin concentration), specific drug release in the agar occurred upon laser exposure and complete bacteria killing was achieved within the irradiated spot. Additionally, a zone of inhibition 6 mm outside the irradiated area was also observed due to drug diffusion within the agar. Significantly, the non-irradiated areas outside the zone of inhibition demonstrated heavy bacterial growth, despite the presence of equally high concentrations of (entrapped) gentamicin throughout the agar. Because even a 10 fold dilution of the gentamicin-PoP-liposomes maintained light-triggered killing (FIG. 13a), the lack of cell killing in the non-irradiated areas of the high concentration dish reflects the stable entrapment efficacy of PoP-liposomes. Control agar plates impregnated with empty PoP-liposomes did not show significant light-triggered antibacterial effect. Thus, gentamicin-PoP liposomes demonstrated efficient spatial control of antibiotic release that may not be achievable as easily or directly using any other triggered release methods. To demonstrate an application for temporal control of cargo release, either free sulforhodamine B or sulforhodamine B-PoP-liposomes were injected intratumorally into nude mice bearing subcutaneous Panc-1 xenografts. Due to their larger size relative to small molecules, liposomes do not drain rapidly drain from tumors following direct injection and for that reason have demonstrated potential as an intratumoral drug delivery vehicle. PoP-liposomes could add a new layer of control to trigger liposomal release following liposomal re-distribution within the tumors. As seen in FIG. 13b, following intratumoral injection of free rhodamine, the molecule rapidly drained from the tumor, with little fluorescence remaining in the tumor 2 hours following injection. Larger nanoparticles (100-200 nm) can be used to significantly slow down the rate of drainage on the order of hours rather than minutes. Sulforhodamine B-PoP-liposomes fall in this size range and were formed with self-quenching concentrations of the fluorophore. 2 hours following intratumoral injection, the tumor was irradiated and released Sulforhodamine B could be clearly visualized following its unquenching. This demonstrated that not only did the size of the liposomes modulate tumor distribution following intratumoral injection, but that the PoP-liposomes were sufficiently stable in vivo to permit release of contents only after light treatment following a 2 hour incubation period.

Active liposomal drug loading makes use of ion and pH gradients to concentrate drugs into the aqueous interior of liposomes. Next, we examined whether active doxorubicin loading was possible using PoP-liposomes, given the stabilizing nature of the porphyrin-doped bilayer. As shown from the gel filtration results in FIG. 14a, doxorubicin could be actively loaded with over 95% efficacy following incubation at 60° C. for 1 hour using an internal ammonium sulfate gradient. FIG. 14b shows that following irradiation, doxorubicin, but not HPPH phospholipid, was released from the PoP-liposomes. When dox-PoP-liposomes were irradiated in a saline buffer including 10% fetal bovine serum, release occurred in both a laser power and irradiation time dose dependent manner (FIG. 14c). It is noteworthy that in addition to varying release characteristics by modulating porphyrin doping and irradiation time, laser power could directly affect release. Over a wide range of fluence rates, doxorubicin release increased with increasing irradiation times (FIG. 21a). Unlike photodynamic therapy, in which higher fluence rates yield lower effects due to depletion of molecular oxygen, complete doxorubicin release from PoP-liposomes depended on total fluence (~85 $J/cm^2$) and the time required for full release could be predicted as a function of fluence rate (FIG. 21b). Unlike phase transition based mechanisms that are constrained to heating target areas to set temperatures, laser power variation adds a powerful new layer of direct control to triggered release. This might be exploited by controlling release into microvessels of specific target sizes since when PoP-liposomes were irradiated in flowing capillary tubing, release was dependent on solution velocity (FIG. 8). Controlled release has upside for doxorubicin in particular since clinical liposomal doxorubicin formulations have been shown to have a slow release rate that results in only 50% bioavailability even after one week in vivo, limiting therapeutic efficacy. FIG. 14d demonstrates that in vitro, there was minimal release from doxorubicin loaded PoP-liposomes throughout the course of a 48 hour incubation in physiological conditions. However, when the sample was subjected to 300 mW, 658 nm laser irradiation, complete release occurred in just 4 minutes. This compares favorably to phase transition-based systems such as thermally-triggered liposomes, which generally exhibit a ~10 fold acceleration in release in physiological conditions when comparing the "on" vs. "off" states. FIG. 14e demonstrates that dox-PoP-liposomes could be used to induce light-triggered inhibition of viability of Panc-1 cells. Laser treatment in the presence or absence of empty PoP-liposomes had no effect on cell viability. Without light treatment, dox-PoP-liposomes, incubated with the cells for 24 hours in 10% serum at 37° C., induced a small amount (~15%) of inhibition of cell viability. This was likely due to some uptake of the drug-loaded liposomes in the extended duration incubation. However, when the dox-PoP-liposomes were treated with 200 $mW/cm^2$ for 5 minutes, significant inhibition (>50%) of cell viability was observed, which was even more effective than the free drug. The reason for superior efficacy of the released doxorubicin compared to the free drug is not clear, but one explanation may be that the free drug bound to serum proteins which impacted cellular uptake, whereas the presence of PoP-liposomes may have interfered with that process. Confocal microscopy revealed that light-triggered release of dox-PoP-liposomes resulted in the doxorubicin becoming bioavailable and translocating to the cell nucleus of Panc-1 pancreatic cancer cells when incubated in serum for 3 hours (FIG. 22).

Next, we investigated mechanistic insights into the properties of light-triggered release. Cryo-TEM revealed that dox-PoP-liposomes contained characteristic fibrous sulfate-doxorubicin crystals within their core (FIG. 15a). Following laser irradiation, not only was doxorubicin released from the PoP-liposomes, but they clearly re-formed with an intact bilayer, providing direct evidence for the propensity for the PoP-liposomes to open and then close in response to NIR light. Further confirming a non-destructive permeabilization mechanism, no change in liposome size, polydispersity and zeta potential was observed following NIR irradiation of dox-PoP-liposomes (FIG. 15b). To test the hypothesis that membranes stably re-sealed following irradiation, calcein-loaded PoP-liposomes were irradiated intermittently, and release during laser "on" and "off" periods was examined in real time. As shown in FIG. 15c, calcein release from liposomes occurred only during irradiation and ceased within seconds of turning the laser off. Negligible release was observed in the periods without laser irradiation. This suggests that PoP-liposomes rapidly re-sealed and re-formed stable bilayers as soon as irradiation was halted, since if permanent destabilization was occurring, some level of background release would be expected immediately following laser stoppage. This provides evidence against a release mechanism is based on covalent chemical photoreaction within the bilayer. Further evidence is shown in FIG. 15d, which demonstrates that NIR laser exposure could be used to induce temporary permeability, with liposomes able to re-seal and entrap external contents. This would not be possible if the laser was inducing reactions that caused permanent lipid bilayer instability. When empty PoP-liposomes were placed in a calcein-containing solution and subjected to laser irradiation, calcein could diffuse into the liposomes and be stably retained there, demonstrating that transient permeabilization could be used to allow loading (as opposed to release) of cargo. Only minimal loading was achieved (0.012% of external calcein), although this could be increased by increasing PoP-liposomes concentration. Under these conditions, minimal (~5%) photobleaching was observed. This represents a novel method for loading of cargo.

The potential utility of dox-PoP-liposomes for systemically-administered therapy was assessed in nude mice bearing subcutaneous KB tumors. Mice were injected with doses of 10 mg/kg dox-PoP-liposomes. 15 minutes following IV injection, tumors were irradiated with 658 nm laser light at 200 $mW/cm^2$ for 12.5 minutes (150 $J/cm^2$), or were not irradiated as a control. 24 hours later, organs were collected and doxorubicin biodistribution was assessed. As shown in FIG. 16a, laser-treatment resulted in the deposition of about 3 fold more doxorubicin compared to non-irradiated tumors, whereas none of the other organs displayed statistically significant differences. Significant enhancement of doxorubicin deposition was noted in other laser-irradiated tissues such as in the skin covering the tumor as well as in muscle that was immediately adjacent to the tumor. This underscores clinical challenges that will necessitate careful light delivery specifically to the tumor, and not to adjacent critical organs. While intratumoral injection followed by irradiation (FIG. 13b) definitively demonstrated that PoP-liposomes are capable of light-triggered release in vivo, the biodistribution results are more complex to interpret. Besides direct drug release, the observed enhancement in tumor doxorubicin deposition could have been influenced by other factors including enhanced tumor permeability due to vascular damage induced by initial drug release and also from photosensitizing effects of the PoP-liposomes during irradiation. It has been demonstrated that PDT using HPPH enhanced tumor deposition of DOXIL® in a murine colon carcinoma model. Future studies will seek to better understand how these multiple factors contribute to enhanced tumor deposition of doxorubicin in PoP-liposomes. Based on the favorable biodistribution results, a survival study was performed based on a single intravenous treatment of dox-PoP-liposomes (10 mg/kg doxorubicin dose). Mice were divided into 4 groups: (1) dox-PoP-liposomes with laser treatment, (2) empty-PoP-liposomes with laser treatment, (3) dox-PoP-liposomes without laser treatment; and (4) saline control. As shown in FIG. 16b, only the dox-PoP-liposomes with laser treatment effectively cured tumors. 4 out of the 5 mice treated had tumors permanently cured with no regrowth after 90 days. Following laser treatment, both dox-PoP-liposomes and empty-PoP-liposomes induced eschar formation on the skin of the tumor, demonstrating that PoP-liposomes themselves have photosensitizing properties. However, the irradiated empty-PoP-liposomes were ineffective at halting tumor growth. Likewise, a single dose of dox-PoP-liposomes without laser treatment was also ineffective at halting tumor growth. Thus, only the laser-treatment of dox-PoP-liposomes was an effective treatment resulting in complete tumor regressions. No treated mice exhibited signs of phototoxicty under ambient lighting (no special housing precautions were taken), and PoP-liposomes are self-quenched while intact.

NMR of HPPH phospholipid

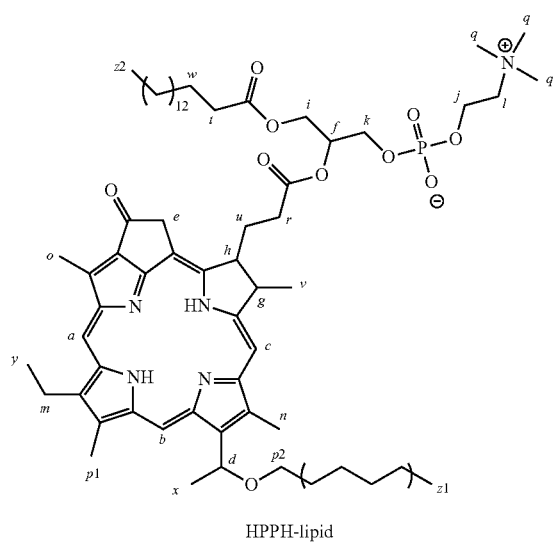

HPPH-lipid $^1$H NMR (500 MHz, CDCl$_3$) δ 9.79(a) (d, J=11.2 Hz, 1H, meso-H), 9.40(b) (s, 1H, meso-H), 8.54(c) (d, J=8.8 Hz, 1H, meso-H), 5.92-5.85(d) (m, 1H, CH(o-hexyl)CH$_3$), 5.36-5.20 (e) (m, 2H, exocyclic ring), 5.13(f) (dd, J=19.7 Hz, 1H, CH(CH$_2$)$_2$), 4.50(g) and 4.30(i) (d, J=6.7 Hz, 2H, COOCH$_2$CH), 4.39(h) (s, 1H, CH(CH)CH$_2$), 4.30(j) (s, 1H, CH(CH)CH$_2$), 4.18-4.06(k) (t, J=12.8, 2H, OCH$_2$CH$_2$), 3.84 (l) (d, J=23.2 Hz, 2H, CH$_2$(CH)(PO$_4$)), 3.66(m) (d, J=7.8 Hz, 2H, CH$_2$(CH$_2$)N(CH$_3$)$_3$), 3.57(n)(m, 2H, CH$_2$CH$_3$), 3.38(o) (s, 3H, C—CH$_3$), 3.33(p) (s, 3H, C—CH$_3$), 3.27(q1) (S, 3H, C—CH$_3$), 3.27(q2) (t, J=11.6, 2H, OCH$_2$), 3.08(r) (s, 9H, N(CH$_3$)$_3$), 2.75(s) (m, 2H, CH$_2$COO), 2.26-2.16(t) (t, J=14.7, 2H, CH$_2$(CH$_2$)COO), 2.11(u) (d, J=6.4 Hz, 2H, CH$_2$(CH)CH$_2$COO), 1.81(v) (dd, J=4.8 Hz, 2H, CH$_2$(CH$_2$) (CH$_2$)$_{12}$), 1.73(w) (d, J=22.4 Hz, 3H, CH$_3$CH), 1.68(x) (t, J=7.5 Hz, 3H, CH$_3$CH$_2$), 1.49(y) (d, J=7.3 Hz, 3H, CH$_3$CH), 1.36-0.95(z) (several H, (CH$_2$)$_{12}$ and (CH$_2$)$_4$), 0.86(al) (t, J=6.9 Hz, 3H, CH$_3$CH$_2$), 0.79(61) (s, 3H, CH$_3$CH$_2$), −1.74 (br, 1H).

In summary, PoP-NVs as described herein form a robust system which achieved thermostable cargo retention as well as effective release upon exposure to clinically-relevant doses of NIR radiation. Release could be tuned by varying porphyrin doping, laser irradiation time and laser irradiation power. This represents a departure from externally-triggered release systems which rely on heating to a few degrees above body temperature and may have issues with stability at physiological temperatures. In response to NIR irradiation, PoP-NVs of the present disclosure released their cargo with robust spatial and temporal control and when loaded with appropriate agents provide effective treatment and diagnostic options.

While the disclosure has been described with reference to specific embodiments, it should be understood by those having skill in the art that various changes in form and detail may be made therein without departing from the spirit and scope of the present disclosure as disclosed herein.

The invention claimed is:

1. A composition comprising nanovesicles, said nanovesicles comprising a bilayer which comprises a porphyrin conjugate having the following structure:

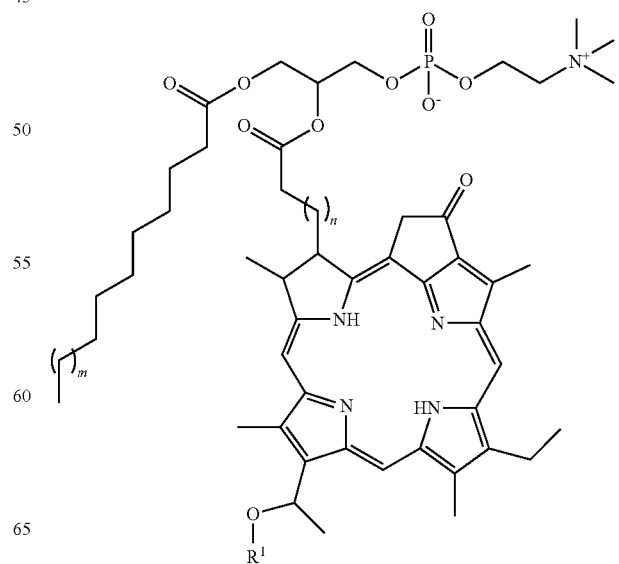

wherein m is an integer from 1 to 12, n is an integer from 1 to 12, and R[1] is a branched or liner alkyl group having from 2 to 20 carbon atoms, wherein the nanovesicle bilayer comprises 0.1 to 14.4 mol. % of the porphyrin conjugate.

2. The composition of claim 1, wherein the porphyrin conjugate is selected from one of the following structures:

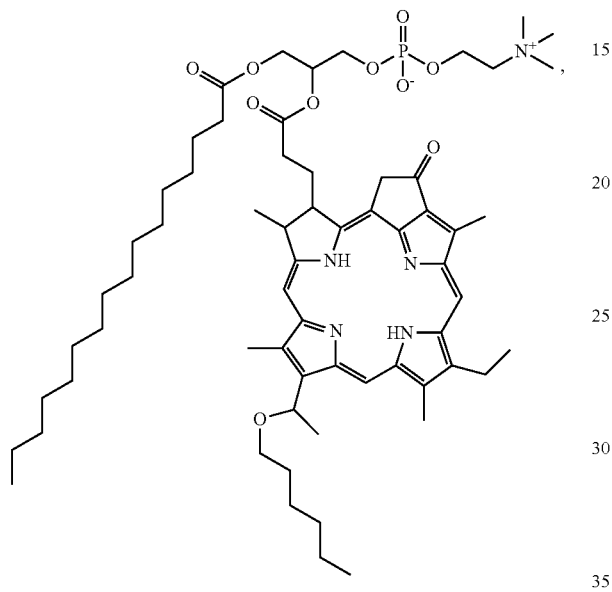

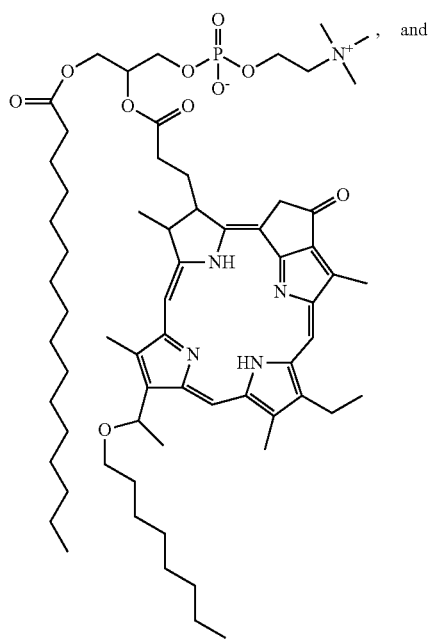

and

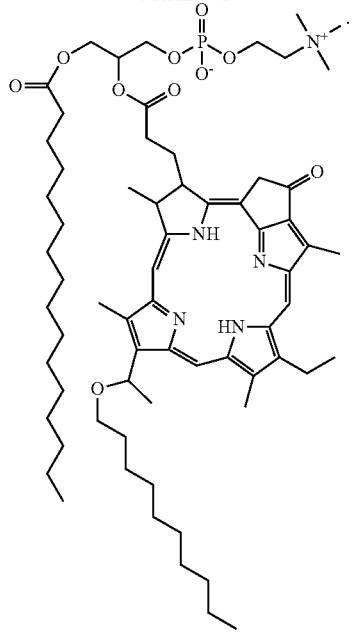

3. The composition of claim 1, wherein the nanovesicles have an average size of 30 to 250 nm.

4. The composition of claim 3, wherein the nanovesicles have an average size of 100 to 175 nm.

5. The composition of claim 1, wherein the nanovesicle bilayer comprises 9.5 to 10.5 mol. % porphyrin conjugate.

6. The composition of claim 1, wherein the bilayer further comprises one or more of distearoyl phosphatidyletha-nolamine (DSPE), DSPE-polyethylene glycol (DSPE-PEG), or cholesterol.

7. The composition of claim 1, wherein the nanovesicles are loaded with cargo, said nanovesicles being releasable after exposure of the nanovesicles to electromagnetic radiation of from 650 to 1000 nm.

8. The composition of claim 7, wherein the cargo comprises a therapeutic agent or a diagnostic agent.

9. The composition of claim 7, wherein the cargo comprises doxorubicin.

10. A method of delivering cargo to a desired location comprising the steps of:
a) administering to an individual the composition of claim 7 such that it enters the circulatory system;
b) allowing the nanovesicles to reach the desired location;
c) exposing the nanovesicles to near infrared radiation of wavelength from 650 to 1000 nm such that the cargo is released from the nanovesicles.

11. The method of claim 10, wherein the composition is administered to the individual via intravenous route.

12. The method of claim 10, wherein the individual is a human or non-human mammal.

13. The method of claim 10, wherein the nanovesicles are exposed to a wavelength of 658, 665, or 671 nm.

14. The method of claim 10, wherein the nanovesicles are exposed to the near infrared radiation for up to 30 minutes.

15. The method of claim 10, wherein step c) is carried out as multiple exposures to the near infrared radiation.

* * * * *